(12) United States Patent
Rios et al.

(10) Patent No.: US 10,500,340 B2
(45) Date of Patent: Dec. 10, 2019

(54) INJECTION SYSTEM

(71) Applicant: TruInject Medical Corp., Irvine, CA (US)

(72) Inventors: Gabrielle A. Rios, Irvine, CA (US); Clark B. Foster, Mission Viejo, CA (US)

(73) Assignee: Truinject Corp., Irvine, CA (US)

( * ) Notice: Subject to any disclaimer, the term of this patent is extended or adjusted under 35 U.S.C. 154(b) by 6 days.

(21) Appl. No.: 15/299,209

(22) Filed: Oct. 20, 2016

(65) Prior Publication Data

US 2017/0136185 A1   May 18, 2017

Related U.S. Application Data

(60) Provisional application No. 62/243,801, filed on Oct. 20, 2015.

(51) Int. Cl.
*A61M 5/31* (2006.01)
*A61M 5/315* (2006.01)
(Continued)

(52) U.S. Cl.
CPC ........ *A61M 5/3129* (2013.01); *A61M 5/3135* (2013.01); *A61M 5/31511* (2013.01); *A61M 5/31566* (2013.01); *A61M 5/486* (2013.01); *G09B 23/285* (2013.01); *A61M 5/31568* (2013.01); *A61M 5/427* (2013.01); *A61M 2205/276* (2013.01); *A61M 2205/332* (2013.01); *A61M 2205/3306* (2013.01); *A61M 2205/3331* (2013.01); *A61M 2205/3375* (2013.01);
(Continued)

(58) Field of Classification Search
CPC .......... A61M 5/31511; A61M 5/31566; A61M 5/486; A61M 5/3135; A61M 5/31568; A61M 5/427; G09B 23/285
See application file for complete search history.

(56) References Cited

U.S. PATENT DOCUMENTS 3,237,340 A   3/1966   Knott
3,941,121 A   3/1976   Olinger et al.
(Continued)

FOREIGN PATENT DOCUMENTS

AU    2011218649 B2    9/2011
AU    2015255197 A1    12/2015
(Continued)

OTHER PUBLICATIONS

Correa et al., "Virtual Reality Simulator for Dental Anesthesia Training in the Inferior Alveolar Nerve Block," Journal of Applied Oral Science, vol. 25, No. 4, Jul./Aug. 2017.
(Continued)

*Primary Examiner* — Theodore J Stigell
(74) *Attorney, Agent, or Firm* — Knobbe, Martens, Olson & Bear, LLP

(57) ABSTRACT

A smart injection system that promotes patient safety includes, among other things, a smart stem that allows for measuring the location of the injection relative to the patient's face and/or the amount of medication injected into the patient. In addition, the smart stem has medication cartridge verification and injector verification features. The smart stem wirelessly transmits the measure data to a processing system.

19 Claims, 16 Drawing Sheets

(51) Int. Cl.
  *A61M 5/48* (2006.01)
  *G09B 23/28* (2006.01)
  *A61M 5/42* (2006.01)

(52) U.S. Cl.
  CPC . *A61M 2205/3389* (2013.01); *A61M 2205/52* (2013.01); *A61M 2205/581* (2013.01); *A61M 2205/582* (2013.01); *A61M 2205/583* (2013.01); *A61M 2205/609* (2013.01); *A61M 2205/6009* (2013.01); *A61M 2205/6054* (2013.01); *A61M 2205/6072* (2013.01); *A61M 2210/0606* (2013.01)

(56) References Cited

U.S. PATENT DOCUMENTS

| | | |
|---|---|---|
| 4,142,517 A | 3/1979 | Contreras Guerrero de Stavropoulos et al. |
| 4,311,138 A | 1/1982 | Sugarman |
| 4,356,828 A | 11/1982 | Jamshidi |
| 4,410,020 A | 10/1983 | Lorenz |
| 4,515,168 A | 5/1985 | Chester et al. |
| 4,566,438 A | 1/1986 | Liese et al. |
| 4,836,632 A | 6/1989 | Bardoorian |
| 4,880,971 A | 11/1989 | Danisch |
| 5,197,476 A | 3/1993 | Nowacki et al. |
| 5,198,877 A | 3/1993 | Schulz |
| 5,241,184 A | 8/1993 | Menzel |
| 5,249,581 A | 10/1993 | Horbal et al. |
| 5,295,483 A | 3/1994 | Nowacki et al. |
| 5,321,257 A | 6/1994 | Danisch |
| 5,391,081 A | 2/1995 | Lampotang et al. |
| 5,518,407 A | 5/1996 | Greenfield et al. |
| 5,622,170 A | 4/1997 | Shulz |
| 5,651,783 A | 7/1997 | Reynard |
| 5,727,948 A | 3/1998 | Jordan |
| 5,817,105 A | 10/1998 | Van Der Brug |
| 5,828,770 A | 10/1998 | Leis et al. |
| 5,890,908 A | 4/1999 | Lampotang et al. |
| 5,899,692 A | 5/1999 | Davis et al. |
| 5,923,417 A | 7/1999 | Leis |
| 5,954,648 A | 9/1999 | Van Der Brug |
| 5,954,701 A | 9/1999 | Matalon |
| 6,024,576 A | 2/2000 | Bevirt et al. |
| 6,061,644 A | 5/2000 | Leis |
| 6,064,749 A | 5/2000 | Hirota et al. |
| 6,127,672 A | 10/2000 | Danisch |
| 6,217,558 B1 | 4/2001 | Zadini et al. |
| 6,288,785 B1 | 9/2001 | Frantz et al. |
| 6,353,226 B1 | 3/2002 | Khalil et al. |
| 6,385,482 B1 | 5/2002 | Boksberger et al. |
| 6,485,308 B1 | 11/2002 | Goldstein |
| 6,553,326 B1 | 4/2003 | Kirsch et al. |
| 6,564,087 B1 | 5/2003 | Pitris et al. |
| 6,575,757 B1 | 6/2003 | Leight et al. |
| 6,625,563 B2 | 9/2003 | Kirsch et al. |
| 6,702,790 B1 | 3/2004 | Ross et al. |
| 6,769,286 B2 | 8/2004 | Biermann et al. |
| 6,774,624 B2 | 8/2004 | Anderson et al. |
| 6,836,745 B2 | 12/2004 | Seiler et al. |
| 6,863,536 B1 | 3/2005 | Fisher et al. |
| 7,015,859 B2 | 3/2006 | Anderson |
| 7,115,113 B2 * | 10/2006 | Evans ............... A61M 5/31533 604/189 |
| 7,137,712 B2 | 11/2006 | Brunner et al. |
| 7,158,754 B2 | 1/2007 | Anderson |
| 7,194,296 B2 | 3/2007 | Frantz et al. |
| 7,204,796 B1 | 4/2007 | Seiler |
| 7,247,149 B2 | 7/2007 | Beyerlein |
| 7,383,728 B2 | 6/2008 | Noble et al. |
| 7,500,853 B2 | 3/2009 | Bevirt et al. |
| 7,553,159 B1 | 6/2009 | Arnal et al. |
| 7,594,815 B2 | 9/2009 | Toly |
| 7,665,995 B2 | 2/2010 | Toly |
| 7,725,279 B2 | 5/2010 | Luinge et al. |
| 7,761,139 B2 | 7/2010 | Tearney et al. |
| 7,783,441 B2 | 8/2010 | Nieminen et al. |
| 7,857,626 B2 | 12/2010 | Toly |
| 7,912,662 B2 | 3/2011 | Zuhars et al. |
| 7,945,311 B2 | 5/2011 | McCloy et al. |
| 8,007,281 B2 | 8/2011 | Toly |
| 8,040,127 B2 | 10/2011 | Jensen |
| 8,072,606 B2 | 12/2011 | Chau et al. |
| 8,131,342 B2 | 3/2012 | Anderson |
| 8,165,844 B2 | 4/2012 | Luinge et al. |
| 8,203,487 B2 | 6/2012 | Hol et al. |
| 8,208,716 B2 | 6/2012 | Choi et al. |
| 8,226,610 B2 | 7/2012 | Edwards et al. |
| 8,250,921 B2 | 8/2012 | Nasiri et al. |
| 8,257,250 B2 | 9/2012 | Tenger et al. |
| 8,277,411 B2 | 10/2012 | Gellman |
| 8,319,182 B1 | 11/2012 | Brady et al. |
| 8,342,853 B2 | 1/2013 | Cohen |
| 8,351,773 B2 | 1/2013 | Nasiri et al. |
| 8,382,485 B2 | 2/2013 | Bardsley |
| 8,403,888 B2 | 3/2013 | Gaudet |
| 8,408,918 B2 | 4/2013 | Hu et al. |
| 8,409,140 B2 | 4/2013 | Ejlersen et al. |
| 8,437,833 B2 | 5/2013 | Silverstein |
| 8,442,619 B2 | 5/2013 | Li et al. |
| 8,450,997 B2 | 5/2013 | Silverman |
| 8,467,855 B2 | 6/2013 | Yasui |
| 8,525,990 B2 | 9/2013 | Wilcken |
| 8,535,062 B2 | 9/2013 | Nguyen |
| 8,556,635 B2 | 10/2013 | Toly |
| 8,632,498 B2 | 1/2014 | Rimsa et al. |
| 8,655,622 B2 | 2/2014 | Yen et al. |
| 8,689,801 B2 | 4/2014 | Ritchey et al. |
| 8,764,449 B2 | 7/2014 | Rios et al. |
| 8,818,751 B2 | 8/2014 | Van Acht et al. |
| 8,917,916 B2 | 12/2014 | Martin et al. |
| 8,945,147 B2 | 2/2015 | Ritchey et al. |
| 8,961,189 B2 | 2/2015 | Rios et al. |
| 8,994,366 B2 | 3/2015 | Ashe |
| 9,017,080 B1 | 4/2015 | Placik |
| 9,024,624 B2 | 5/2015 | Brunner |
| 9,031,314 B2 | 5/2015 | Clausen et al. |
| 9,251,721 B2 | 2/2016 | Lampotang et al. |
| 9,439,653 B2 | 9/2016 | Avneri et al. |
| 9,443,446 B2 | 9/2016 | Rios et al. |
| 9,456,766 B2 | 10/2016 | Cox et al. |
| 9,460,638 B2 | 10/2016 | Baker et al. |
| 9,486,162 B2 | 11/2016 | Zhuang et al. |
| 9,626,805 B2 | 4/2017 | Lampotang et al. |
| 9,792,836 B2 | 10/2017 | Rios et al. |
| 9,922,578 B2 | 3/2018 | Foster et al. |
| 2002/0168618 A1 | 11/2002 | Anderson et al. |
| 2003/0031993 A1 | 2/2003 | Pugh |
| 2003/0055380 A1 | 3/2003 | Flaherty |
| 2003/0108853 A1 | 6/2003 | Chosack et al. |
| 2003/0114842 A1 | 6/2003 | DiStefano |
| 2004/0009459 A1 | 1/2004 | Anderson et al. |
| 2004/0092878 A1 | 5/2004 | Flaherty |
| 2004/0118225 A1 | 6/2004 | Wright et al. |
| 2004/0175684 A1 | 9/2004 | Kaasa et al. |
| 2005/0055241 A1 | 3/2005 | Horstmann |
| 2005/0057243 A1 | 3/2005 | Johnson et al. |
| 2005/0084833 A1 | 4/2005 | Lacey et al. |
| 2005/0181342 A1 | 8/2005 | Toly |
| 2006/0084050 A1 | 4/2006 | Haluck |
| 2006/0194180 A1 | 8/2006 | Bevirt et al. |
| 2006/0264745 A1 | 11/2006 | Da Silva |
| 2007/0003917 A1 | 1/2007 | Kitching et al. |
| 2007/0179448 A1 * | 8/2007 | Lim ............... A61M 5/1452 604/187 |
| 2007/0197954 A1 | 8/2007 | Keenan |
| 2007/0238981 A1 | 10/2007 | Zhu |
| 2008/0097378 A1 | 4/2008 | Zuckerman |
| 2008/0107305 A1 | 5/2008 | Vanderkooy et al. |
| 2008/0138781 A1 | 6/2008 | Pellegrin et al. |
| 2008/0176198 A1 | 7/2008 | Ansari et al. |
| 2009/0043253 A1 * | 2/2009 | Podaima ............... G16H 10/60 604/67 |
| 2009/0046140 A1 | 2/2009 | Lashmet |

(56) References Cited

U.S. PATENT DOCUMENTS

| | | |
|---|---|---|
| 2009/0061404 A1 | 3/2009 | Toly |
| 2009/0081619 A1 | 3/2009 | Miasnik |
| 2009/0081627 A1 | 3/2009 | Ambrozio |
| 2009/0123896 A1 | 5/2009 | Hu et al. |
| 2009/0142741 A1 | 6/2009 | Ault et al. |
| 2009/0208915 A1 | 8/2009 | Pugh |
| 2009/0263775 A1 | 10/2009 | Ullrich |
| 2009/0265671 A1 | 10/2009 | Sachs et al. |
| 2009/0278791 A1 | 11/2009 | Slycke et al. |
| 2009/0305213 A1 | 12/2009 | Burgkart et al. |
| 2009/0326556 A1 | 12/2009 | Diolaiti |
| 2010/0030111 A1 | 2/2010 | Perriere |
| 2010/0071467 A1 | 3/2010 | Nasiri et al. |
| 2010/0099066 A1 | 4/2010 | Mire et al. |
| 2010/0120006 A1 | 5/2010 | Bell |
| 2010/0167249 A1 | 7/2010 | Ryan |
| 2010/0167254 A1 | 7/2010 | Nguyen |
| 2010/0179428 A1 | 7/2010 | Pederson et al. |
| 2010/0198141 A1 | 8/2010 | Laitenberger et al. |
| 2010/0273135 A1 | 10/2010 | Cohen |
| 2011/0027767 A1 | 2/2011 | Divinagracia |
| 2011/0046915 A1 | 2/2011 | Hol et al. |
| 2011/0071419 A1 | 3/2011 | Liu et al. |
| 2011/0202012 A1* | 8/2011 | Bartlett ............... A61M 5/3287 604/218 |
| 2011/0207102 A1 | 8/2011 | Trotta et al. |
| 2011/0236866 A1 | 9/2011 | Psaltis et al. |
| 2011/0257596 A1 | 10/2011 | Gaudet |
| 2011/0269109 A2 | 11/2011 | Miyazaki |
| 2011/0294103 A1 | 12/2011 | Segal et al. |
| 2011/0301500 A1 | 12/2011 | Maguire et al. |
| 2012/0015336 A1 | 1/2012 | Mach |
| 2012/0026307 A1 | 2/2012 | Price |
| 2012/0034587 A1 | 2/2012 | Toly |
| 2012/0130269 A1 | 5/2012 | Rea |
| 2012/0148994 A1 | 6/2012 | Hori et al. |
| 2012/0171652 A1 | 7/2012 | Sparks et al. |
| 2012/0214144 A1 | 8/2012 | Trotta et al. |
| 2012/0219937 A1 | 8/2012 | Hughes |
| 2012/0238875 A1 | 9/2012 | Savitsky et al. |
| 2012/0251987 A1 | 10/2012 | Huang et al. |
| 2012/0280988 A1 | 11/2012 | Lampotang et al. |
| 2012/0282583 A1 | 11/2012 | Thaler et al. |
| 2012/0301858 A1 | 11/2012 | Park et al. |
| 2012/0323520 A1 | 12/2012 | Keal |
| 2013/0018494 A1 | 1/2013 | Amini |
| 2013/0046489 A1 | 2/2013 | Keal |
| 2013/0100256 A1 | 4/2013 | Kirk et al. |
| 2013/0131503 A1 | 5/2013 | Schneider et al. |
| 2013/0179110 A1 | 7/2013 | Lee |
| 2013/0189658 A1 | 7/2013 | Peters et al. |
| 2013/0197845 A1 | 8/2013 | Keal |
| 2013/0198625 A1 | 8/2013 | Anderson |
| 2013/0203032 A1 | 8/2013 | Bardsley |
| 2013/0236872 A1 | 9/2013 | Laurusonis et al. |
| 2013/0267838 A1 | 10/2013 | Fronk et al. |
| 2013/0296691 A1 | 11/2013 | Ashe |
| 2013/0323700 A1 | 12/2013 | Samosky |
| 2014/0102167 A1 | 4/2014 | MacNeil et al. |
| 2014/0120505 A1 | 5/2014 | Rios et al. |
| 2014/0121636 A1 | 5/2014 | Boyden |
| 2014/0162232 A1 | 6/2014 | Yang et al. |
| 2014/0212864 A1 | 7/2014 | Rios et al. |
| 2014/0240314 A1 | 8/2014 | Fukazawa et al. |
| 2014/0244209 A1 | 8/2014 | Lee et al. |
| 2014/0260704 A1 | 9/2014 | Lloyd et al. |
| 2014/0278183 A1 | 9/2014 | Zheng et al. |
| 2014/0278205 A1 | 9/2014 | Bhat et al. |
| 2014/0278215 A1 | 9/2014 | Keal et al. |
| 2014/0349266 A1 | 11/2014 | Choi |
| 2015/0079545 A1 | 3/2015 | Kurtz |
| 2015/0104773 A1 | 4/2015 | Toly et al. |
| 2015/0182706 A1 | 7/2015 | Wurmbauer et al. |
| 2015/0206456 A1 | 7/2015 | Foster et al. |
| 2015/0262512 A1 | 9/2015 | Rios et al. |
| 2015/0352294 A1 | 12/2015 | O'Mahoney et al. |
| 2015/0379899 A1 | 12/2015 | Baker et al. |
| 2015/0379900 A1 | 12/2015 | Samosky et al. |
| 2016/0000411 A1 | 1/2016 | Raju et al. |
| 2016/0001016 A1 | 1/2016 | Poulsen et al. |
| 2016/0155363 A1 | 6/2016 | Rios et al. |
| 2016/0193428 A1 | 7/2016 | Perthu |
| 2016/0213856 A1 | 7/2016 | Despa et al. |
| 2016/0293058 A1 | 10/2016 | Gaillot et al. |
| 2016/0374902 A1* | 12/2016 | Govindasamy ....... A61J 7/0436 604/155 |
| 2017/0178540 A1 | 6/2017 | Rios et al. |
| 2017/0186339 A1 | 6/2017 | Rios et al. |
| 2017/0245943 A1 | 8/2017 | Foster et al. |
| 2017/0252108 A1 | 9/2017 | Rios et al. |
| 2017/0254636 A1 | 9/2017 | Foster et al. |
| 2018/0012516 A1 | 1/2018 | Rios et al. |
| 2018/0197441 A1 | 7/2018 | Rios et al. |
| 2018/0211562 A1* | 7/2018 | Rios .................. A61M 5/31511 |
| 2018/0240365 A1 | 8/2018 | Foster et al. |
| 2018/0261125 A1 | 9/2018 | Rios et al. |
| 2018/0261126 A1 | 9/2018 | Rios et al. |

FOREIGN PATENT DOCUMENTS

| | | |
|---|---|---|
| CA | 2865236 A1 | 9/2013 |
| CN | 2751386 Y | 1/2006 |
| CN | 201213049 Y | 3/2009 |
| CN | 102708745 A | 10/2012 |
| CN | 104703641 A | 6/2015 |
| CN | 105118350 A | 12/2015 |
| CN | 205541594 U | 8/2016 |
| CN | 106710413 A | 5/2017 |
| CN | 107067856 A | 8/2017 |
| DE | 202005021286 U1 | 9/2007 |
| EP | 0316763 A1 | 5/1989 |
| EP | 1504713 A1 | 2/2005 |
| EP | 1723977 A1 | 11/2006 |
| EP | 1884211 A2 | 2/2008 |
| EP | 2538398 A1 | 12/2012 |
| EP | 2425416 B1 | 3/2015 |
| EP | 2756857 B1 | 5/2016 |
| GB | 2288686 B | 7/1997 |
| GB | 2309644 A | 8/1997 |
| GB | 2508510 | 6/2014 |
| IN | 201202900 P1 | 11/2013 |
| JP | 2013-037088 A | 2/2013 |
| JP | 52-21420 | 6/2013 |
| JP | 2013-250453 A | 12/2013 |
| JP | 2014-153482 A | 8/2014 |
| KR | 2012009379 | 2/2012 |
| KR | 20140047943 A | 4/2014 |
| TW | 201207785 A | 2/2012 |
| WO | WO 00/53115 | 9/2000 |
| WO | WO 02/083003 | 10/2002 |
| WO | WO 2005/083653 | 9/2005 |
| WO | WO 2007/109540 | 9/2007 |
| WO | WO 2008/005315 A2 | 1/2008 |
| WO | WO 2008/122006 A1 | 10/2008 |
| WO | WO 2009/023247 A1 | 2/2009 |
| WO | WO 2009/049282 | 4/2009 |
| WO | WO 2009/094646 | 7/2009 |
| WO | WO 2009/141769 | 11/2009 |
| WO | WO 2011/043645 | 4/2011 |
| WO | WO 2011/127379 | 10/2011 |
| WO | WO 2011/136778 | 11/2011 |
| WO | WO 2012/075166 | 6/2012 |
| WO | WO 2012/088471 A1 | 6/2012 |
| WO | WO 2012/101286 | 8/2012 |
| WO | WO 2012/106706 | 8/2012 |
| WO | WO 2012/155056 | 11/2012 |
| WO | WO2012/155056 * | 11/2012 |
| WO | WO 2013/025639 | 2/2013 |
| WO | WO 2013/064804 A1 | 5/2013 |
| WO | WO 2014/070799 | 5/2014 |
| WO | WO 2014/100658 | 6/2014 |
| WO | WO 2015/109251 | 7/2015 |
| WO | WO 2015/110327 A1 | 7/2015 |
| WO | WO 2015/136564 | 9/2015 |

(56) References Cited

FOREIGN PATENT DOCUMENTS

| WO | WO 2015/138608 | 9/2015 |
|---|---|---|
| WO | WO 2015/171778 | 11/2015 |
| WO | WO 2016/089706 | 6/2016 |
| WO | WO 2016/123144 A2 | 8/2016 |
| WO | WO 2016/162298 | 10/2016 |
| WO | WO 2016/191127 | 12/2016 |
| WO | WO 2017/048929 A1 | 3/2017 |
| WO | WO 2017/048931 A1 | 3/2017 |
| WO | WO 2017/050781 A1 | 3/2017 |
| WO | WO 2017/060017 A1 | 4/2017 |
| WO | WO 2017/070391 | 4/2017 |
| WO | WO 2017/151441 | 9/2017 |
| WO | WO 2017/151716 | 9/2017 |
| WO | WO 2017/151963 | 9/2017 |
| WO | WO 2017/153077 | 9/2017 |
| WO | WO 2018/136901 | 7/2018 |

OTHER PUBLICATIONS

Garg et al., "Radial Artery cannulation—Prevention of pain and Techniques of cannulation: review of literature," The Internet Journal of Anesthesiology, vol. 19, No. 1, 2008, in 6 pages.
International Search Report and Written Opinion for Appl. No. PCT/US2017/019518, dated Sep. 18, 2017, 19 pages.
Jafarzadeh et al., "Design and construction of an automatic syringe injection pump," Pacific Science Review A: Natural Science and Engineering 18, 2016, in 6 pages.
Kettenbach et al., "A robotic needle-positioning and guidance system for CT-guided puncture: Ex vivo results," Minimally Invasive Therapy and Allied Technologies, vol. 23, 2014, in 8 pages.
Ladjal, et al., "Interactive Cell Injection Simulation Based on 3D Biomechanical Tensegrity Model," 2008 IEEE/RSJ International Conference on Intelligent Robots and Systems, in 9 pages.
Lee et al., "An Intravenous Injection Simulator Using Augmented Reality for Veterinary Education and its Evaluation," Proceedings of the 11th ACM SIGGRAPH International Conference on Virtual-Reality Continuum and its Applications in Industry, Dec. 2-4, 2012, in 4 pages.
Poyade et al., "Development of a Haptic Training Simulation for the Administration of Dental Anesthesia Based Upon Accurate Anatomical Data," Conference and Exhibition of the European Association of Virtual and Augmented Reality, 2014, in 5 pages.
Quio, "Smartinjector," available at https://web.archive.org/web/20161017192142/http://www.quio.com/smartinjector, Applicant believes to be available as early as Oct. 17, 2016, in 3 pages.
State Electronics, "Sensofoil Membrane Potentiometer," Product Information and Technical Specifications.
Truinject Corp., "Smart Injection Platform," http://truinject.com/technology/, in 3 pages.
Desjardins, et al. "Epidural needle with embedded optical fibers for spectroscopic differentiation of tissue: ex vivo feasibility study", Biomedical Optics Express, vol. 2(6): pp. 1-10. Jun. 2011.
"The EpiAccess System: Access with Confidence", EpiEP Epicardial Solutions, dated 2015, in 2 pages.
Afzal, et al., "Use of Earth's Magnetic Field for Mitigating Gyroscope Errors Regardless of Magnetic Perturbation," Sensors 2011, 11, 11390-11414; doi:10.3390/s111211390, 25 pp. published Nov. 30, 2011.
Andraos et al., "Sensing your Orientation" Address 2007, 7 pp.
Arms, S.W., "A Vision for Future Wireless Sensing Systems," 44 pp., 2003.
Bao, et al., "A Novel Map-Based Dead-Reckoning Algorithm for Indoor Localization", J. Sens. Actuator Netw, 2014, 3, 44-63; doi:10.3390/jsan3010044, 20 pp., Jan. 3, 2014.
Benbasat et al., "An Inertial Measurement Framework for Gesture Recognition and Applications," I. Wachsmuth and T. Sowa (Eds.): GW 2001, Springer-Verlag Berlin Heidelberg, 12 pp., 2002.
Brunet et al., "Uncalibrated Stereo Vision," A CS 766 Project, University of Wisconsin—Madison, 6 pp, Fall 2004, http://pages.cs.wisc.edu/~chaol/cs766/.
Brunet et al., "Uncalibrated Stereo Vision," A CS 766 Project, University of Wisconsin—Madison, 13 pp, Fall 2004, http://pages.cs.wisc.edu/~chaol/cs766/.
Esteve, Eric, "Why do you need 9D Sensor Fusion to support 3D orientation?", 5 pp., Aug. 23, 2014, https://www.semiwiki.com/forum/content/3794-why-do-you-need-9d-sensor-fusion-support-3d-orientation.html.
Grenet et al., "spaceCoder: a Nanometric 3D Position Sensing Device," CSEM Scientific & Technical Report, 1 page, 2011.
Inition. Virtual Botox: Haptic App Simulated Injecting the Real Thing. Retrieved from http://inition.co.uk/case-study/virtual-botox-haptic-app-simulates-injecting-real-thing.
International Search Report and Written Opinion for Appl. No. PCT/US2013/067352 dated Mar. 31, 2014 in 10 pages.
International Search Report and Written Opinion for Appl. No. PCT/US2015/011845, dated Apr. 29, 2015 in 10 pages.
International Search Report and Written Opinion for Appl. No. PCT/US2015/019974, dated May 21, 2015, 10 pages.
International Search Report and Written Opinion for Appl. No. PCT/US2015/062798, dated Mar. 14, 2016, 12 pages.
Madgwick, Sebastian O.H., "An efficient orientation filter for inertial and inertial/magnetic sensor arrays," 32 pp., Apr. 30, 2010.
Microsoft, "Integrating Motion and Orientation Sensors," 85 pp., Jun. 10, 2013.
Miller, Nathan L., Low-Power, Miniature Inertial Navigation System with Embedded GPS and Extended Kalman Filter, MicroStrain, Inc., 12 pp., 2012.
MPU-9150 9-Axis Evaluation Board User Guide, Revision 1.0, 15 pp., May 11, 2011, http//www.invensense.com.
MPU-9150, Register Map and Descriptions, Revision 4.2, 52 pp., Sep. 18, 2013, http//www.invensense.com.
MPU-9150, Product Specification, Revision 4.3, 50 pp., Sep. 18, 2013, http//www.invensense.com.
PST Iris Tracker, Plug and Play, 3D optical motion tracking specifications, 1 p., Dec. 4, 2014, www.pstech.com.
PST Iris Tracker, Instruction Manual, 3D optical motion tracking specifications, 42 pp., Jul. 27, 2012, www.pstech.com.
Search and Examination Report for Appl. No. GB1319193.7 in 6 pages dated Mar. 28, 2014.
Search and Examination Report, dated Feb. 23, 2015, by the UK Intellectual Property Office, in the matter of Application No. GB1414892.8 of TruInject Medical Corporation, 6 pp.
Struik, Pieter, "Ultra Low-Power 9D Fusion Implementation: A Case Study," Synopsis, Inc., 7 pp., Jun. 2014.
Sutherland, et al. "An Augmented Reality Haptic Training Simulator for Spinal Needle Procedures," IEEE, 2011.
Varesano, Fabio, "Prototyping Orientation and Motion Sensing Objects with Open Hardware," Dipartimento di Informatica, Univ. Torino, http://www.di.unito.it/~varesano, Feb. 10, 2013, 4 pp.
Varesano, Fabio, "FreeIMU: An Open Hardware Framework for Orientation and Motion Sensing," Dipartimento di Informatica, Univ. Torino, http://www.di.unito.it/~varesano, Mar. 20, 2013, 10 pp.
"B-Smart disposable manometer for measuring peripheral nerve block injection pressures", Bbraun USA, 2016.
Bergamini et al., "Estimating Orientation Using Magnetic and Inertial Sensors and Different Sensor Fusion Approaches: Accuracy Assessment in Manual and Locomotion Tasks", Oct. 2014, 18625-18649.
"EPGL Medical Invents Smart Epidural Needle, Nerve Ablation and Trigger Point Treatment Devices: New Smart Medical Devices Will Give Physicians Advanced Situational Awareness During Critical Procedures," EPGL Medical, dated Aug. 12, 2013, in 3 pages. Retrieved from http://www.prnewswire.com/news-releases/epgl-medical-invents-smart-epidural-needle-nerve-ablation-and-trigger-point-treatment-devices-219344621.html#.
Helen, L., et al. "Investigation of tissue bioimpedance using a macro-needle with a potential application in determination of needle-to-nerve proximity", Proceedings of the 8th International Conference on Sensing Technology, Sep. 2-4, 2014, pp. 376-380.
International Search Report and Written Opinion for Appl. No. PCT/US2016/057974, dated Apr. 19, 2017, 21 pages.

(56) References Cited

OTHER PUBLICATIONS

Kalvøy, H., et al., "Detection of intraneural needle-placement with multiple frequency bioimpedance monitoring: a novel method", Journal of Clinical Monitoring and Computing, Apr. 2016, 30(2):185-192.

"A beginner's guide to accelerometers," Dimension Engineering LLC, accessed Jul. 11, 2018, in 2 pages, https://www.dimensionengineering.com/info/accelerometers.

"Accelerometer: Introduction to Acceleration Measurement," Omega Engineering, Sep. 17, 2015, 3 pages, https://www.omega.com/prodinfo/accelerometers.html.

International Preliminary Report on Patentability for Appl. No. PCT/US2016/057974, dated May 3, 2018, 13 pages.

* cited by examiner

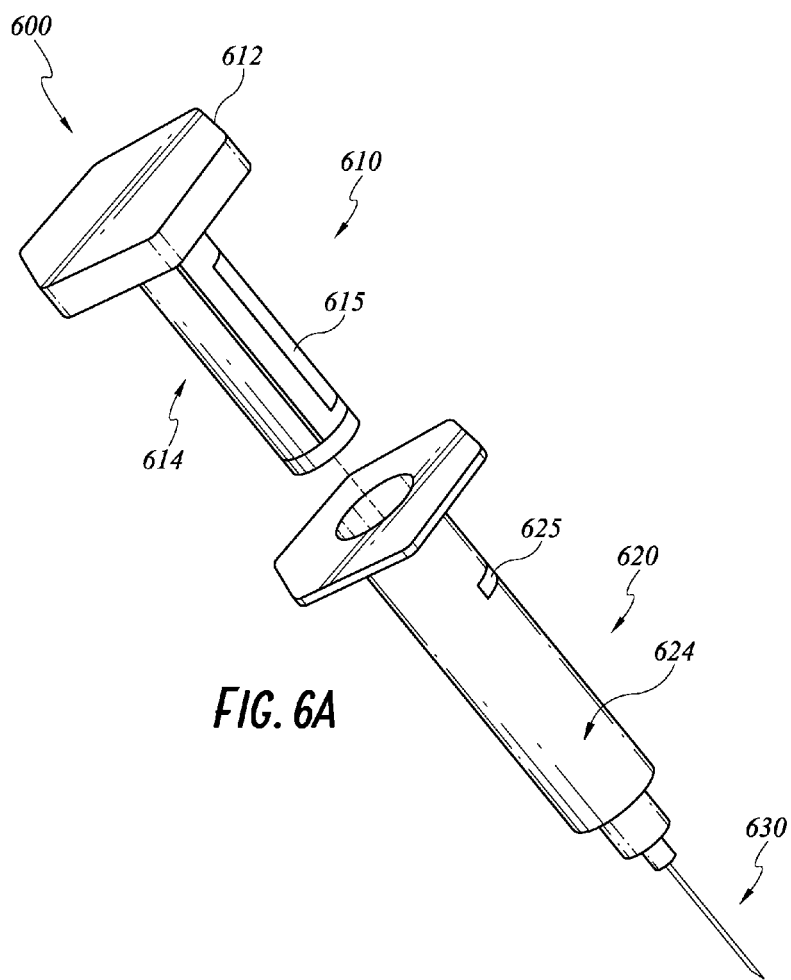

INJECTION SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. Specifically, this application claims U.S. Provisional Application No. 62/243,801, filed Oct. 20, 2015 and entitled "INJECTION SYSTEM," the entirety of which is hereby incorporated by reference and should be considered a part of this specification.

FIELD

The present disclosure is related to a smart injection system. In particular, the present disclosure is related to a smart injection system that promotes patient safety.

BACKGROUND

A variety of medical injection procedures are often performed in prophylactic, curative, therapeutic, or cosmetic treatments. Injections may be administered in various locations on the body, such as under the conjunctiva, into arteries, bone marrow, the spine, the sternum, the pleural space of the chest region, the peritoneal cavity, joint spaces, and internal organs. Injections can also be helpful in administering medication directly into anatomic locations that are generating pain. These injections may be administered intravenously (through the vein), intramuscularly (into the muscle), intradermally (beneath the skin), subcutaneously (into the fatty layer of skin) or intraperitoneal injections (into the body cavity). Injections can be performed on humans as well as animals. The methods of administering injections typically range for different procedures and may depend on the substance being injected, needle size, or area of injection.

Injections are not limited to treating medical conditions, but may be expanded to treating aesthetic imperfections, restorative cosmetic procedures, procedures for treating migraine, depression, epidurals or other therapeutic procedures. Many of these procedures are performed through injections of various products into different parts of the body. The aesthetics and therapeutic industry consists of two main categories of injectable products: neuromodulators and dermal fillers. The neuromodulator industry commonly utilizes nerve-inhibiting products such as Botox®, Dysport®, and Xeomin®. The dermal filler industry utilizes products administered by providers to patients for both cosmetic and therapeutic reasons, such as, for example, Juvederm®, Restylane®, Belotero®, Sculptra®, Artefill®, and others. These providers or injectors may include plastic surgeons, facial plastic surgeons, oculoplastic surgeons, dermatologists, primary care givers, psychologist/psychiatrist, nurse practitioners, dentists, and nurses.

SUMMARY OF THE DISCLOSURE

Patient safety is of utmost importance in any injection procedure. One measure for ensuring patient safety is to train caregivers to have steady hands and provide the procedure in compliance with standard safety protocol. Some aspects of the disclosure are directed toward a smart injection system that can aid the caregiver in complying with the safety protocol. For example, the present disclosure provides features allowing for monitoring of an injection speed, aiding in locating the intended injection site, and facilitating injection of hyaluronidase at the last injection site when an artery occlusion occurs.

Another measure is to have an injection system with verification features to alert the caregiver and/or patient about counterfeit, and potentially unsafe, medication or other aspects of the injection treatment that are not in compliance with the standard of care. For example, the smart injection system is configured to read information about the manufacturer, serial/lot number, expiration date, and the like. Some aspects of the disclosure are directed toward a smart injection system allowing for components of the injection system to be authenticated to ensure that the patient is not receiving counterfeit or expired, therefore potentially unsafe, medication. The manufacturer can also receive the information about the medications actually used in patients from the injection system. The injection system can further allow identification of the injector to ensure that the person providing the injection is qualified to carry out the procedure.

An embodiment of an injection system can include a reusable electronic assembly configured to be coupled to at least a portion of a disposable syringe. The syringe can include at least a stem, a barrel and a needle. The electronic assembly can be configured to measure at least one of injection force and/or pressure, injection speed, displacement of the stem relative to the barrel, a volume of medication injected, medication flow rate, position and movement of the stem and/or the syringe relative to a patient's face, biometric data of a person performing the injection, and/or indication of authenticity of medication. The electronic assembly can be configured to communicate with a hardware processor that is configured to process the measured data. In some embodiments, the injection system can further comprise a syringe that includes a stem having a proximal cap and a shaft. The stem shaft is configured to engage a lumen of a barrel from a proximal end of the barrel and a distal end of the barrel is configured to couple to a needle. The needle is configured to penetrate skin of a patient to inject medication contained in the syringe to a patient. In some embodiments, the syringe is disposable. In some embodiments, the hardware processor is configured to provide analysis of the measured data. In some embodiments, the electronic assembly further comprises a wireless data transmitter. In some embodiments, at least a portion of the electronic assembly is located on a snap-on data cap configured to be coupled with the proximal cap of the stem. In some embodiments, at least a portion of the electronic assembly is built into the proximal cap of the stem. In some embodiments, at least a portion of the electronic assembly is built into a removable flange configured to be coupled with the barrel at or near a proximal end of the barrel. In some embodiments, the hardware processor is on a remote server.

In some embodiments of the injection system, the injection speed, displacement of the stem relative to the syringe, volume of medication injected, and/or medication flow rate is measured by a displacement sensor located on or near a distal end of the proximal cap of the stem, the displacement sensor configured to send one or more acoustic or optical signals to a reflecting surface on the barrel and receive one or more reflected acoustic or optical signals. In some embodiments, the reflecting surface is on a proximal flange of the barrel. In some embodiments, the reflecting surface is on a friction collar circumferentially surrounding a portion of the stem shaft. In some embodiments, the injection speed, displacement of the stem relative to the syringe, volume of medication injected, and/or medication flow rate is measured by a resistance reader on the stem shaft. In some embodiments, the output of the hardware processor further comprises a warning that is at least one of audio, visual, or tactile feedback when the desired amount of displacement has been achieved and/or when the rate of displacement falls outside a desired range.

In some embodiments, the injection force and/or pressure is measured by a force or pressure sensor located on the proximal cap of the stem, the force or pressure sensor configured to measure data about a force or pressure applied on the proximal cap. In some embodiments, the output of the hardware processor further comprises a warning that is at least one of audio, visual, or tactile feedback when the measured force or pressure fall outside a desired range. In some embodiments, the force and/or pressure, injection speed, displacement of the stem relative to the syringe, volume of medication injected, or medication flow rate is measured by a velocity sensor. In some embodiments, the hardware processor is configured to process the measured injection pressure and medication flow rate to output an indication that an injection site is an artery.

In some embodiments of the injection system, the position and movement of the syringe relative to a patient's face is measured by an angular, rotational and positioning sensor, the angular, rotational and positioning sensor configured to interact with one or more landmarks on a patient's face to measure data about a location of the syringe relative to the patient's face. In some embodiments, the landmarks comprise at least one of a pair of glasses, a mouth guard, stickers or ink markings configured to be placed on the patient's face. In some embodiments, the output of the hardware processor further comprise a warning that is at least one of audio, visual, or tactile feedback when the syringe is targeting a no-injection zone or an indication that the syringe is targeting an approved zone.

In some embodiments of the injection system, the biometric data of the person performing the injection is measured by a fingerprint reader. In some embodiments, the output of the hardware processor further comprise a warning that is at least one of audio, visual, or tactile feedback when the biometric data does not match one qualified to perform the injection, the hardware processor having access to a database of qualified personnel.

In some embodiments of the injection system, the indication of authenticity of medication is measured by an identification device on the barrel and a corresponding identification device reader on the stem shaft, the corresponding identification device reader interacting with the identification device when the stem is pushed distally into the barrel lumen. In some embodiments, the identification device is one or more of an EEPROM, a barcode, an RFID tag and a resistor. In some embodiments, the identification device is on the barrel shaft. In some embodiments, the identification device is near a proximal opening to the barrel lumen. In some embodiments, the indication of authenticity of medication is measured by an identification device on a lip of the barrel and a corresponding identification device reader on a removable flange, the corresponding identification device reader interacting with the identification device when the removable flange couples with the barrel lip. In some embodiments, the processor is configured to compare the data measured by the identification device reader with a database. In some embodiments, the indication of authenticity of medication comprises one or more of manufacturer's information, product type, serial number, lot number, date of expiration, prior use of the syringe, instructions for use, or indications. In some embodiments, the output of the hardware processor further comprise a warning that is at least one of audio, visual, or tactile feedback when the medication is counterfeit, has expired, and/or the barrel has been used before.

An embodiment of a method of promoting patient safety during an injection procedure can be used with an injection system including a disposable syringe assembly and a reusable electronic assembly. The method can include sending from the electronic assembly including a displacement sensor on a stem or a barrel of the disposable syringe assembly one or more acoustic or optical signals in a direction substantially parallel to a longitudinal axis of the stem when the stem shaft is moving distally inside a lumen of the barrel, receiving at the displacement sensor one or more signals reflected from a reflecting surface on the barrel or the stem, and calculating displacement and/or rate of displacement of the stem relative to the barrel based on the time lapse between sending and receiving each signal. In some embodiments, the reflecting surface is on a proximal flange of the barrel. In some embodiments, the reflecting surface is on a friction collar circumferentially surrounding a portion of the stem shaft.

In some embodiments, the method further comprises communicating with a hardware processor to send measured data about the displacement and/or rate of displacement to the hardware processor. In some embodiments, the communicating with the hardware processor is performed via a wireless data transmitter on the injection system. In some embodiments, the method further comprises measuring a force or pressure applied when the stem shaft is pushed distally inside the barrel lumen using the electronic assembly including a force or pressure sensor, wherein the force or pressure sensor is located on the stem.

Another embodiment of a method of promoting patient safety during an injection procedure can be used with an injection system including a disposable syringe assembly and a reusable electronic assembly. The method can include measuring, using the reusable electronic assembly, a speed of a movement of a stem shaft of the disposable syringe assembly relative to a barrel of the disposable syringe assembly when the stem shaft moves distally inside a lumen of the barrel; and calculating for display purposes, based on the measured speed, one or more of injection force and/or pressure, injection speed, displacement of the stem relative to the barrel, a volume of medication injected, or medication flow rate. In some embodiments, the method further comprises determining a relationship of the measured force or pressure and the rate of displacement and outputting a warning that is audio, visual, or tactile feedback when the relationship indicates that the needle is in an artery.

Another embodiment of a method of medication verification can be used with an injection system including a disposable syringe assembly and a reusable electronic assembly. The method can include coupling a shaft of a stem of the disposable syringe assembly with a lumen of a barrel of the disposable syringe assembly, the barrel including an identification device containing information specific to a prefilled medication and/or the syringe containing the prefilled medication, the stem shaft including an identification device reader, and moving the stem shaft toward a distal end of the barrel, wherein the identification device reader is configured to read data from the identification device and communicate the data to a hardware processor configured to process the read data and output an indication related to information about the medication and/or the barrel. In some embodiments, the verification device includes encoded information specific to the prefilled medication and/or the syringe. In some embodiments, the verification device is one or more of one or more of an EEPROM, a barcode, an RFID tag and a resistor. In some embodiments, the information specific to the prefilled medication and/or syringe comprise one or more of manufacturer's information, product type, serial number, lot number, date of expiration, prior use of the barrel, instructions for use, and/or indications.

Another embodiment of a method of medication verification can be used with an injection system including a disposable syringe assembly and a reusable electronic assembly. The method can include coupling a removable flange to a lip of a barrel of the disposable syringe assembly, the barrel including an identification device containing information specific to a prefilled medication and/or the syringe containing the prefilled medication, the flange including an identification device reader. The identification device reader is configured to read data from the identification device when the removable flange is coupled to the lip of the barrel and communicate the data to a hardware processor configured to process the read data and output an indication related to information about the medication and/or the barrel. In some embodiments, the verification device includes encoded information specific to the prefilled medication and/or the syringe. In some embodiments, the verification device is one or more of one or more of an EEPROM, a barcode, an RFID tag and a resistor. In some embodiments, the information specific to the prefilled medication and/or syringe comprise one or more of manufacturer's information, product type, serial number, lot number, date of expiration, prior use of the barrel, instructions for use, and/or indications.

Another embodiment of a method of promoting patient safety during an injection procedure can be used with an injection system including a disposable syringe assembly and a reusable electronic assembly. The method can include receiving at a hardware processor data from a 9-axis IMS of the reusable electronic assembly located on the disposable syringe assembly, receiving at the hardware processor information about one or more landmarks on a patient's face, the one or more landmarks defining the patient's face. calculating a location and position of the injection system relative to a patient's face, and outputting an indication when the injection system is targeting an approved injection zone or a no-injection zone. In some embodiments, the 9-axis IMS is located on data cap coupled to a proximal cap of a stem of the disposable syringe assembly. In some embodiments, the 9-axis IMS is located on a proximal cap of a stem of the disposable syringe assembly. In some embodiments, the 9-axis IMS is located on a removable flange coupleable to a lip of a barrel of the disposable syringe assembly.

Another embodiment of an injection system includes a reusable memory device configured to be coupled to a portion of a syringe assembly, the syringe assembly including at least a barrel, a stem and a needle. A memory device reader is configured to read data from the memory device and communicate the data to a hardware processor configured to process the read data and output an indication related to information about a medication held by the barrel and/or the syringe assembly. In some embodiments, the barrel contains prefilled medication. In some embodiments, the syringe assembly is disposable. In some embodiments, the memory device is on a shaft of the barrel. In some embodiments, the memory device is on a lip on a proximal end of the barrel. In some embodiments, the memory device is one or more of one or more of an EEPROM, a barcode, an RFID tag and a resistor. In some embodiments, the data on the memory device comprise one or more of manufacturer's information, product type, serial number, lot number, date of expiration, prior use of the barrel, instructions for use, and/or indications.

Another embodiment of an injection system includes a reusable memory device reader configured to be coupled to at least a portion of a syringe assembly, the syringe assembly including at least a stem, a barrel and a needle. The memory device reader is configured to read data from a memory device located on the barrel and communicate the data to a hardware processor configured to process the read data and output an indication related to information about the medication and/or the barrel. In some embodiments, the barrel contains prefilled medication. In some embodiments, the syringe assembly is disposable. In some embodiments, the memory device reader is on a shaft of the stem, wherein coupling the stem with the barrel allows the memory device reader to interact with the memory device on the barrel. In some embodiments, the memory device reader is on a proximal cap of the stem, wherein coupling the stem with the barrel allows the memory device reader to interact with the memory device on the barrel. In some embodiments, the memory device reader is on a reusable flange configured to be removably coupled to a lip of the barrel, wherein coupling the flange to the lip of the barrel allows the memory device reader to interact with the memory device located on the lip of the barrel. In some embodiments, the memory device reader is a reader for one or more of an EEPROM, a barcode, an RFID tag and a resistor. In some embodiments, the data on the memory device comprise one or more of manufacturer's information, product type, serial number, lot number, date of expiration, prior use of the barrel, instructions for use, and/or indications.

Another embodiment of an injection system includes a reusable memory device configured to be coupled to a barrel of a syringe assembly and a reusable memory device reader configured to be coupled to at least a portion of the syringe assembly. The syringe assembly can further include at least a stem and a needle. The memory device reader is configured to read data from the memory device located on the barrel and communicate the data to a hardware processor configured to process the read data and output an indication related to information about the medication and/or the barrel. In some embodiments, the barrel contains prefilled medication. In some embodiments, the syringe assembly is disposable. In some embodiments, the memory device is on a shaft of the barrel. In some embodiments, the memory device is on a lip on a proximal end of the barrel. In some embodiments, the memory device is one or more of one or more of an EEPROM, a barcode, an RFID tag and a resistor. In some embodiments, the data on the memory device comprise one or more of manufacturer's information, product type, serial number, lot number, date of expiration, prior use of the barrel, instructions for use, and/or indications. In some embodiments, the memory device reader is on a shaft of the stem, wherein coupling the stem with the barrel allows the memory device reader to interact with the memory device on the barrel. In some embodiments, the memory device reader is on a proximal cap of the stem, wherein coupling the stem with the barrel allows the memory device reader to interact with the memory device on the barrel. In some embodiments, the memory device reader is on a reusable flange configured to be removably coupled to a lip of the barrel, wherein coupling the flange to the lip of the barrel allows the memory device reader to interact with the memory device located on the lip of the barrel.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 6A illustrates an embodiment of a smart injection system with an identification device on a syringe and an identification device reader on a stem.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Some aspects of this present disclosure are directed to a smart injection system having smart features, that can, among other things, allow for measuring the location of the injection relative to the patient's face, guide the caregiver to the last injection site, measure the amount of medication injected into the patient and/or the speed and/or force of injection, authenticate medication to be injected in the patient, and verify identification of the injection provider.

Overview of Electronic Assembly

Figure 1:
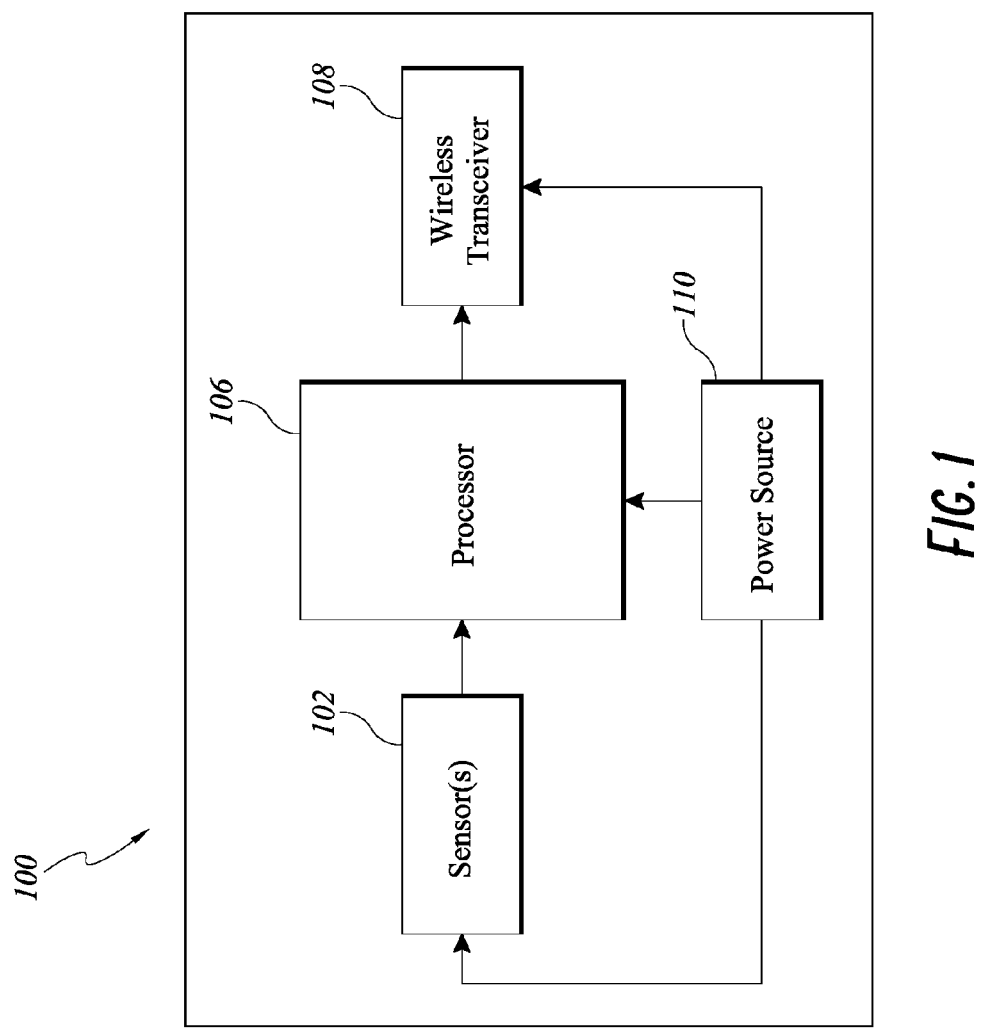
FIG. 1 is a simplified functional block diagram of an embodiment of the electronics assembly 100 of the smart syringe.

In some embodiments, a smart injection system includes a stem, a syringe, a needle, and an electronics assembly. The smart features of the injection system can be provided by interaction of the electronic assembly with at least one of the stem, syringe, needle assembly, or the patient. The smart injection system can wirelessly transmit measured data to a processing system that processes the data and to further transmit the data to one or more remote servers. FIG. 1 illustrates schematically an example electronics assembly 100 of a smart syringe. Physical locations and configurations of components of the electronics assembly 100 can vary and will be described in detail below.

As shown in FIG. 1, the electronics assembly 100 can include one or more sensors/readers 102, a processor 106, a wireless transceiver 108, and a power source (e.g., a battery) 110. The sensors/readers 102 that can be integrated into the electronic assembly are not limiting and can be any sensor or reader known in the art. Some examples include position sensor, force/pressure sensor, proximity/displacement sensor, biometric sensor, velocity sensor, resistance reader, barcode reader, EEPROM reader, or RFID tag reader. The position sensor can be accelerometer, gyroscope and magnetometer with three-degree angular and three-degree rotational resolution, and with a sensor drift adjustment capability (pitch, yaw and roll). The force sensor can be capable of sensing up to twenty pounds (20 lbs.) of force with a 2 percent accuracy factor. The proximity/displacement sensor can be optic range sensors or acoustic sensors. One example of an optic range sensor is a time-of-flight (ToF) camera system such as the FlightSense™ Ranging products (STMicroelectronics, Geneva Switzerland). One example of an acoustic range sensor is an ultrasonic sensor. A skilled artisan will appreciate that numerous other sensors and readers can be used in the disclosed electronics assembly 100 without departing from the scope of the disclosure herein. In some embodiments the electronics assembly 100 communicates data by way of a wireless transceiver 108 employing, for example, a Bluetooth wireless communications protocol. Other forms of wireless communication can also be used.

In some embodiments, the stem, syringe, and needle assembly of the smart injection system can be off-the-shelf or any standard injection systems, with the electronic assembly attached to one or more of the stem, syringe, and needle assembly before use. These embodiments can advantageously promote compatibility with most standard injection systems. The standard injection systems can be disposable, which can prevent cross-contamination due to re-use of any of the needle, syringe, or stem. In other embodiments, the stem 210, syringe 220, and needle assembly 230 can be custom-made to fit the electronic assembly 100. More details of these embodiments will be described below.

Data Cap with Force/Pressure Sensor

Figure 2A:
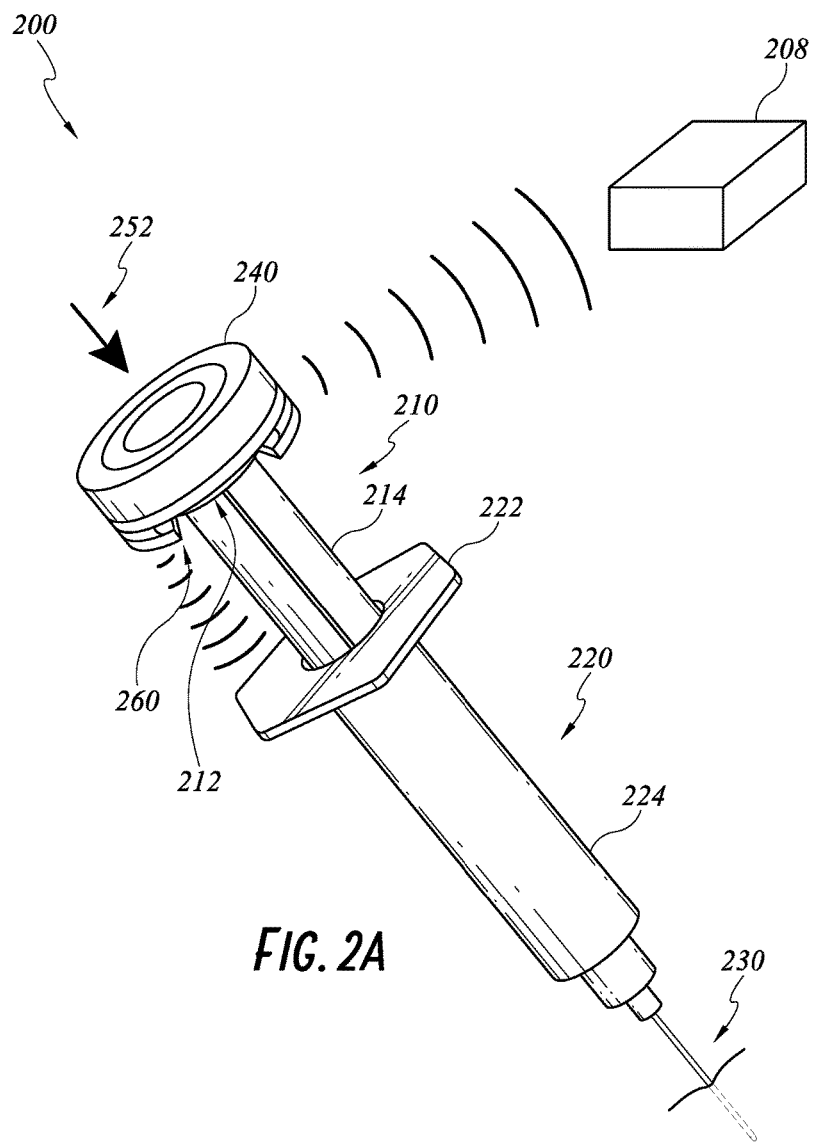
FIG. 2A illustrates an embodiment of a smart injection system with a data cap.

FIG. 2A illustrates a smart injection system 200 including the electronic assembly described above, a stem 210, a syringe 220, and a needle 230. In FIG. 2A, the stem 210, syringe 220, and needle 230 can be any standard injection systems with no built-in electronic components or smart features. The electronics assembly is attached to the standard injection system. For example, the electronic assembly can be built into a data cap 240, which can be coupled with a proximal cap 212 of the stem 210, making it a smart stem 210. The data cap 240 can be battery operated or rechargeable. One non-limiting example of coupling the data cap 240 and the proximal cap 212 of the stem 210 is a snap-fit feature. More detailed structures of the data cap 240 is shown in a cross sectional view of the injection system 200 in FIG. 2B. The data cap 240 can have an integrated cap 242 sliding over a cap body 244. The cap body 244 can have a slot 246 configured to accommodate the proximal cap 212 of the stem 210. A skilled artisan will appreciate that other means of coupling can be used, such as adhesives or clips. The electronic components, such as sensor(s)/reader(s), power source, and/or wireless transmitters can be built into an enclosed space formed by the integrated cap 242 and the cap body 244.

Figure 2B:
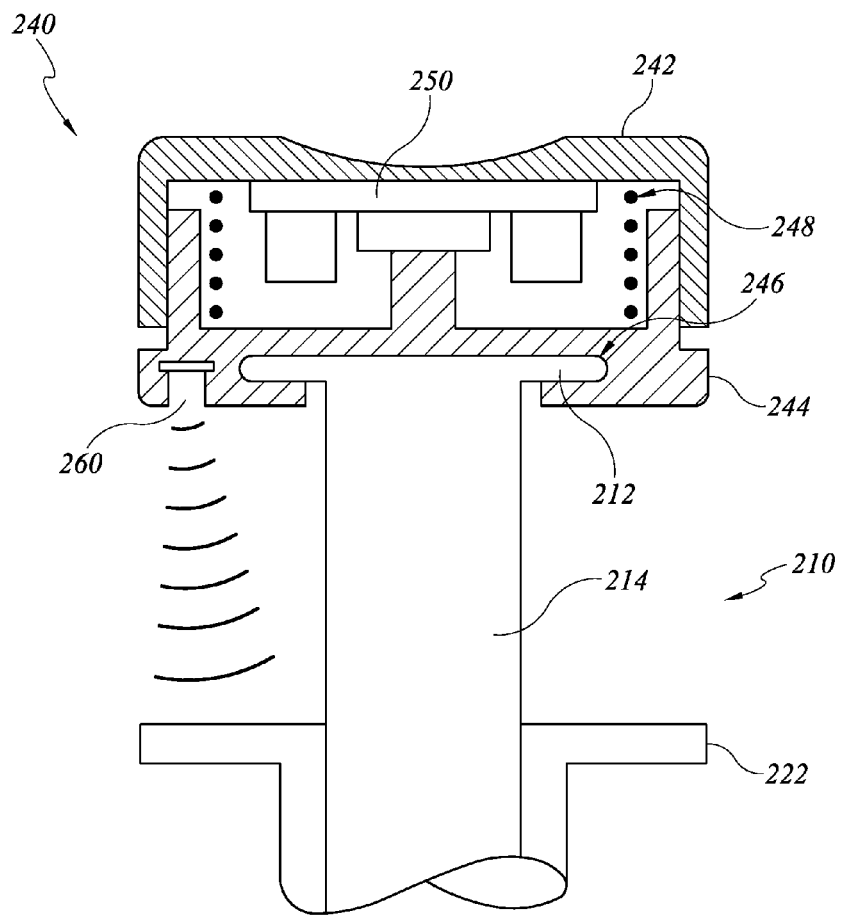
FIG. 2B illustrates a cross section of a proximal portion of the smart injection system of FIG. 2A.

The data cap 240 can incorporate a printed circuit board (PCB) 250 having a force/pressure sensor. As illustrated in FIG. 2B, the PCB 250 can be located on a flat surface under a proximal end of the integrated cap 242 of the data cap 240. More specifically, the PCB 250, and therefore the force/pressure sensor is sandwiched between the flat surface of the integrated cap 242 and a column on the cap body 244. When the caregiver pushes the stem 210 distally along the syringe shaft 224 toward the needle 230, forces applied to the integrated cap 242 are transmitted to the proximal cap 212 via the force/pressure sensor and the column. The data cap 240 can optionally have a return spring 248 biased against an expanded configuration of the data cap 240 when no force is applied on the data cap 240. Pushing onto the data cap 240 can compress the return spring 248 and cause the data cap 240 to transit to a compressed configuration. The return spring 248 can advantageously maintain a minimum height of the enclosed space, preventing the electrical components inside the enclosed space from touching an inner surface of the cap body 244.

When a shaft 214 of the stem is positioned within a syringe shaft 224 and the caregiver pushes 252 onto the data cap 240, the stem shaft 214 is constrained to move distally and proximally along a longitudinal axis of the syringe shaft 224. The force/pressure sensor can measures a force or pressure applied to the data cap 240, which is the force or pressure applied to inject medication in the syringe 220. The force/pressure sensor can communicate the measured force/pressure information to, for example, an external processing system such as an interface/display device, by way of a communications protocol. In some embodiments the force/pressure sensor communicates data by way of the wireless transceiver 208 employing, for example, a Bluetooth wireless communications protocol. In some embodiments, the force/pressure sensor communicates data by way of a USB port using a cable that has a minimal diameter and is highly compliant.

In some embodiments, warnings can be given by the smart injection system 100, or the wireless transceiver 208 when the force/pressure measured by the force/pressure sensor exceeds or falls below a predetermined range. The form of warning is non-limiting, and can be audio, visual or tactile. By way of example, a beep or buzz can alert the caregiver and the patient of an inappropriate injection force/pressure. In another example, only a flashing LED light can go off or the smart injection system 200 can send a signal to, for example, a wristwatch worn by the caregiver, to provide tactile feedback. The visual and tactile alerts will only alert the caregiver so as to not agitate the patient during the injection procedure.

An ability of the smart injection system to measure the injection force/pressure can advantageously help in training the caregiver or medical personnel in providing a steady and desired injection force/pressure. A steady and appropriate injection force/pressure can reduce discomfort to the patient and ensure patient safety. Different medications may have different viscosity and require different ranges of injection force/pressure. The information about suitable ranges of injection force/pressure for various medications can be prepopulated in a processor of the wireless transceiver 208 before using the data cap 240. The information can also be encoded in a memory device included in the body of the syringe 220 during manufacturing and read by the data cap 240. For example, it can be in the form of an RFID tag, a bar code, a resistance value or encoded in an EPROM. In one embodiment, when the stem 210 and the data cap 240 coupled to the stem 210 are connected to the syringe 220, an electrical circuit can be completed such that the data cap 240 can communicate with any wired memory device on the syringe 220.

Data Cap with Displacement Sensor

With continued reference to FIGS. 2A-B, the data cap 240 can include a displacement sensor 260 as described herein. The displacement sensor 260 can be on a distal end of the data cap 240 such as when the data cap 240 is coupled to the proximal cap 212 of the stem 210, the displacement sensor 260 is at a distal side of the proximal cap 212. As shown in FIG. 2B, the displacement sensor 260 can be located on an outer surface of the cap body 244 of the data cap and directly faces a reflecting surface of a proximal syringe flange 222.

Figure 2C:
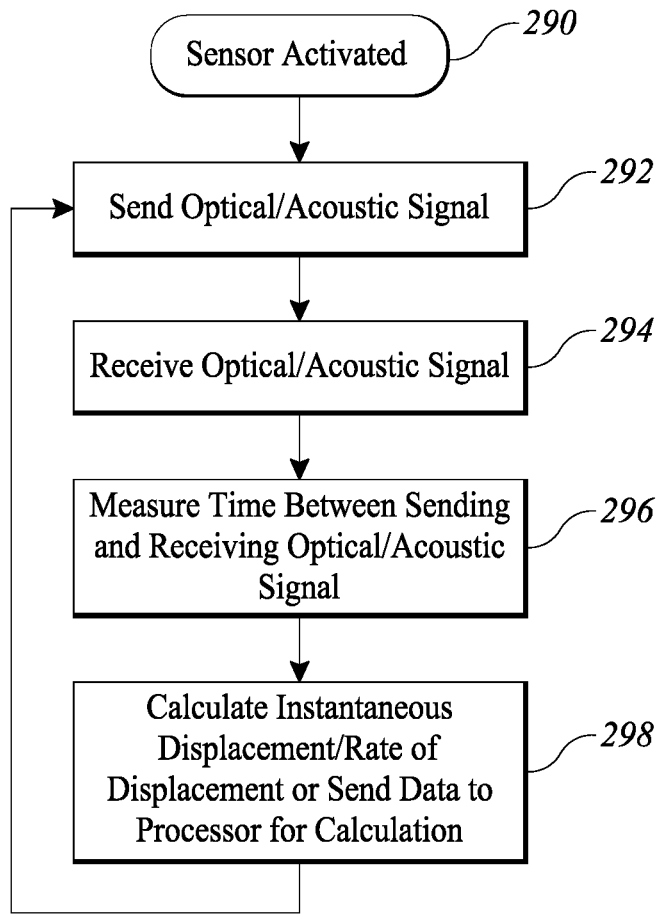
FIG. 2C illustrates an example flowchart of displacement/rate of displacement measurement by an embodiment of a smart injection system.

When the caregiver pushes onto the data cap 240, and therefore the proximal cap 212 of the stem 210, the displacement sensor 260 can detect axial travel/displacement of the stem shaft 212 within the syringe shaft 224. In some embodiments, the displacement sensor 260 detects a displacement of the stem shaft 212 with respect to time. As shown in FIG. 2C, the displacement sensor 260, such as the FlightSense™ sensor or an ultrasound sensor, can be activated 290 in any manner known in the art. For example, the sensor can be activated by charged or when the stem 210 connects to the syringe 220. The displacement sensor can be activated when the electronic assembly of the stem is charged. The activated displacement sensor 260 can send a signal 292 toward the proximal flange 222 of the syringe 220 and receive the signal 294 when the signal returns upon hitting a reflecting surface on the proximal flange 222 facing the displacement sensor 260. The displacement sensor 260 can measure and record 296 the time taken between sending and receiving the signal. The displacement sensor 260 can then communicate the measured data to a processor or the wireless transceiver 208 in the manner described herein. The processor can calculate an instantaneous displacement or rate of displacement of the stem 210 relative to the syringe 220 by taking into account the speed of light or sound as the displacement sensor 260 repeats the steps 292, 294, 296 to provide the processor with data measured with respect to subsequent signals. A skilled artisan will appreciate any types of optic range sensor or acoustic sensors can measure the displacement or rate of displacement of the stem 210 relative to the syringe 220.

Information about the displacement and/or the rate of displacement of the stem 210 can be valuable. For example, the information can be used to inform the medical personnel and/or the patient that the injection speed is too high or too low. In addition, as an inner cross sectional area of the syringe shaft 220 can be known, the displacement of the stem 210 inside the syringe shaft 224 can be used to calculate a volume of the medication being injected into the patient. In some embodiments, the information about the volume of injected medication can be available to the caregiver, patient, and or manufacturers of the medication real time. In some embodiments, the information can be automatically sent to the patient, manufacturer, medical professional, or a repository. This information can provide assurance to the patient that an appropriate amount of medication has been provided. The information can incentivize the caregiver to comply with injection procedure because detailed information about how the injection procedure is performed can be recorded and be part of the patient's medical record. The information also provides the medication manufacturers with a tool for inventory keeping and for predicting future sales. Current technology allows the manufacturers to only keep track of the amount of medication sold, but not of the amount of medication actually used.

Figure 2D:
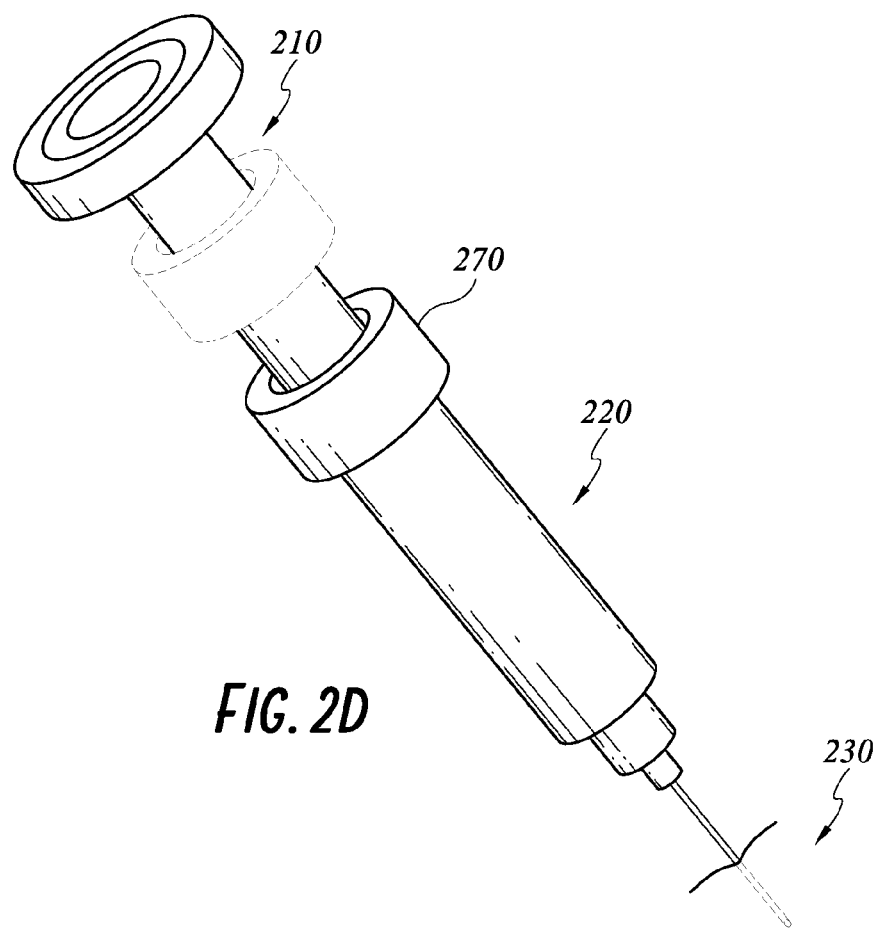
FIG. 2D illustrates another embodiment of the smart injection system with a friction collar on a shaft of a smart stem.

Alternative embodiments of the injection system capable of measuring displacement and/or displacement rate of the stem 210 relative to the syringe 220 will now be described. FIG. 2D illustrates an optional friction slide collar 270, which can have a surface with reflective property facing the proximal cap 212 of the stem. This surface can function as a reflecting surface instead of the syringe flange 222. The collar can move axially along the stem shaft 214 and can advantageously provide more fine-tuned resolution for axial displacement or rate of displacement of the stem 210 relative to the syringe 220 as the collar does not move or wobble when the stem 210 is moved axially into the syringe.

Figure 2E:
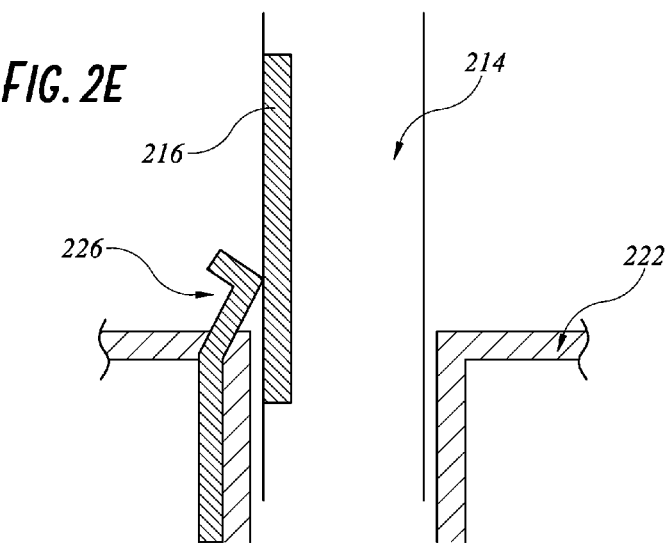
FIG. 2E illustrates another embodiment of a smart injection system with a resistance wiper feature.

FIG. 2E illustrates another method of measuring displacement and/or displacement rate of the stem 210 relative to the syringe 220. In this embodiment, the syringe 220 has a spring wiper 226 at or near a proximal end of the syringe 220. For example, the wiper 226 can be located right above the syringe flange 222. The stem shaft 214 has a strip of variable resistor 216 along a longitudinal axis of the stem shaft 214. The resistor 216 can be electrically wired to the wireless communication components on the stem 210 and can provide measured resistance values to the wireless transceiver 208. The measured resistance values can inform on the axial displacement or displacement rate of the stem 210 relative to the syringe 220. Further, any combination of the above-described displacement sensors can be used in a single device.

Data Cap with Force/Pressure and Displacement Sensors

Figure 3:
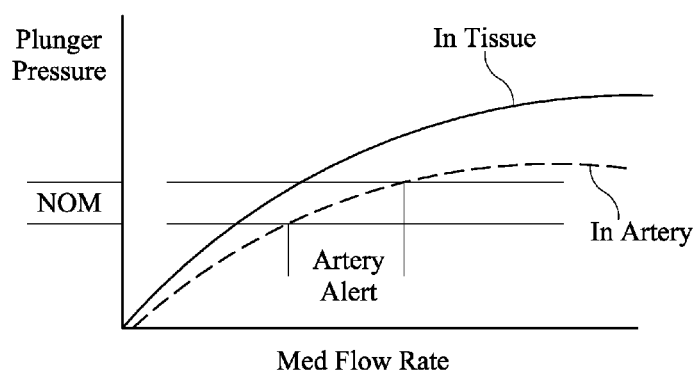
FIG. 3 illustrates stem pressure versus medication flow rate in tissue and in artery of any embodiment of a smart injection system.

Turning to FIG. 3, a method of an embodiment of a smart injection system having both a force/pressure sensor and a displacement sensor disclosed herein will now be described. A risk during an injection procedure is when the needle hits an artery, because the medication injected can lead to artery occlusion, and can potentially cause blindness in the patient. One or more processors, such as one on a remote server, in communication with the smart injection system or included as part of the smart injection system, can process measured data from included sensors. For example, the one or more processors can analyze pressure applied to the stem in relation to a mediation flow rate. The flow rate can be calculated from the displacement rate data as described above. The relationships of the pressure applied on the stem and the medication flow rate when the needle is placed in the tissue and inside an artery are illustrated in FIG. 3. The processor can analyze the medication flow rate when the pressure measured by the force/pressure sensor is within a nominal range. As shown in FIG. 3, the flow rate is significantly higher in the artery than in the tissue for the same range of nominal pressure because blood has less resistance than tissues.

Using this information, the processor can output a warning in any manner as described herein when the flow rate during the nominal range of measured pressure indicated that the current injection site is an artery instead of tissue. This will warn a physician to stop the injection immediately and can provide immediate instructions for applying a dissolving agent. The immediate alert can also allow the physician to leave the needle in place and swap the currently injected substance for a dissolving agent without changing the injection site. In some embodiments, when the needle is still inside the artery, the syringe containing the medication can be replaced with a syringe containing a clot-dissolving agent. A non-limiting example of a clot-dissolving agent is hyaluronidase.

Data Cap with Angular & Relative Positioning

Returning to FIGS. 2A-B, the data cap 240 can include 3-axis gyroscope, 3-axis accelerometer, and 3-axis magnetometer (a 9-axis Inertia Motion Sensor (IMS)) as described herein. The 9-axis IMS can measure angular position and rotation of the data cap 240, and therefore of the proximal cap 212 of the stem 210. As shown in FIG. 2B, the 9-axis IMS can be located on the PCB 250, although a skilled artisan will recognize that the 9-axis IMS can be located in any appropriate part of the data cap 240.

Figure 4A:
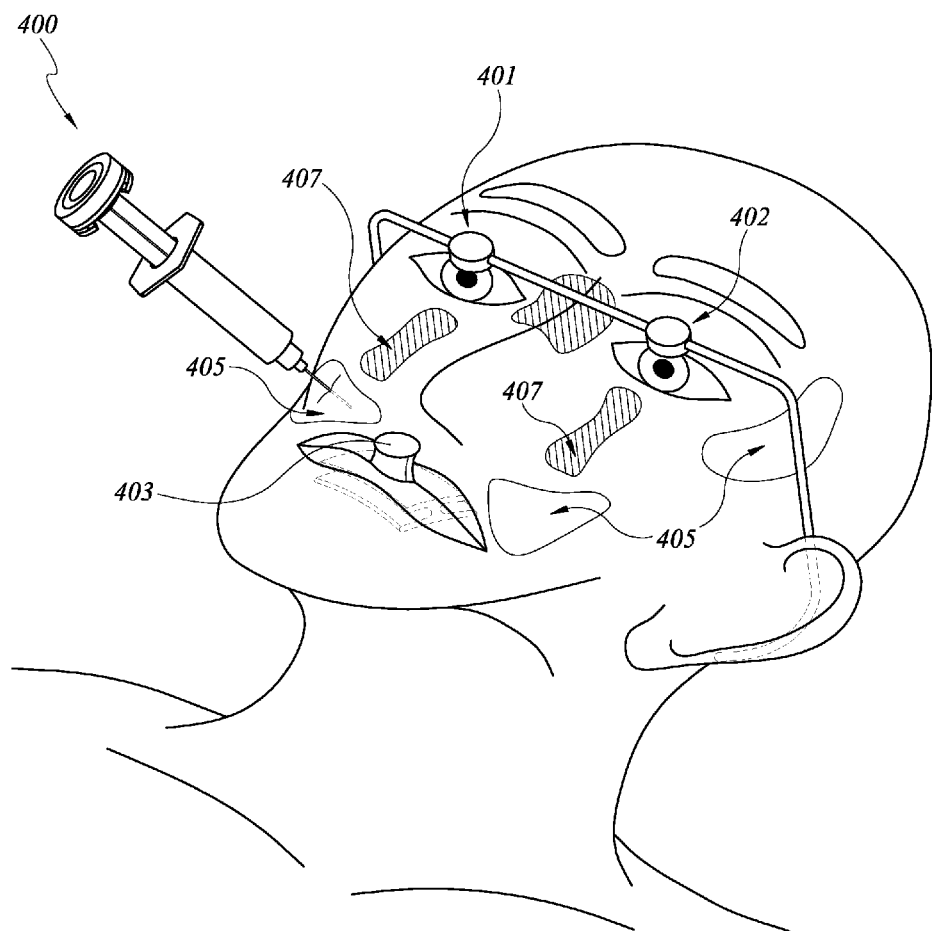
FIG. 4A illustrates another embodiment of a smart injection system with features for monitoring location of an injection site relative to the patient's face.
Figure 4B:
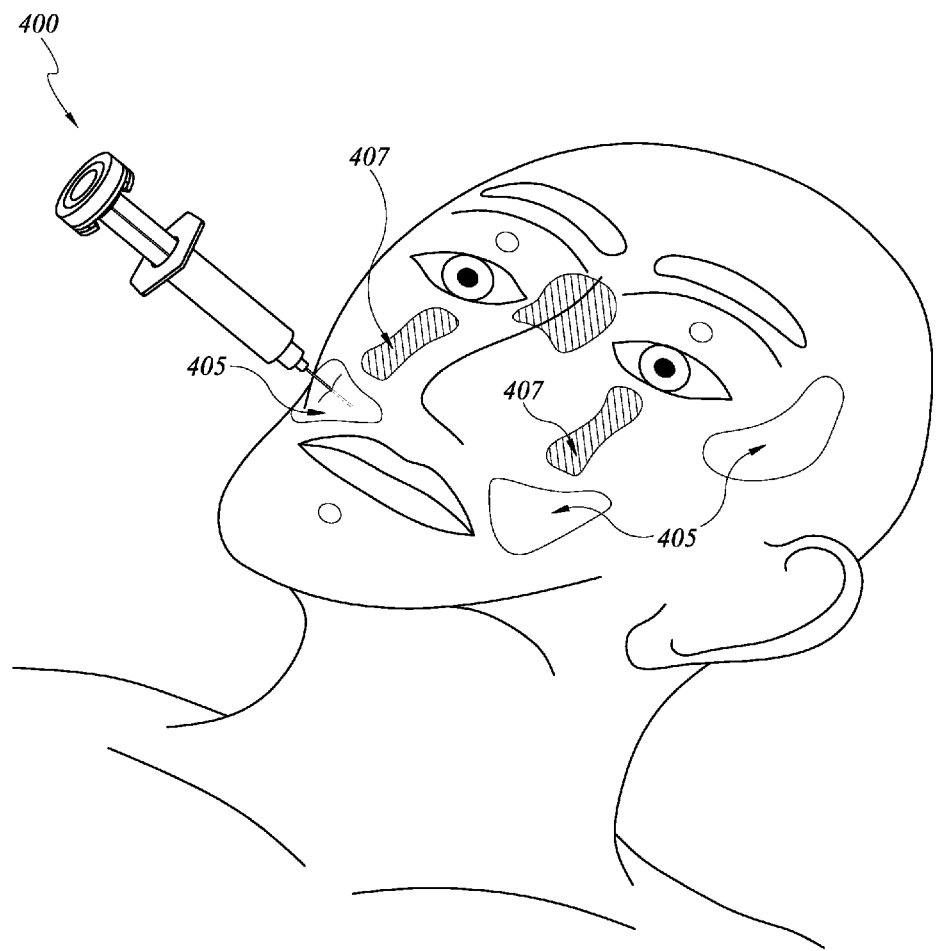
FIG. 4B illustrates an example flowchart of location determination by an embodiment of a smart injection system.

Methods of using a smart injection system 400 having a 9-axis IMS for locating approved and/or prohibited injection zone(s) will be described with reference to FIGS. 4A-C. As shown in FIG. 4A, two landmarks 401, 402 on a patient's face can be provided on a pair of glasses and a third landmark 403 can be identified provided a bite block on a patient's mouth to define a patient's face. A skilled artisan will appreciate that any suitable landmarks of any combination can be used to define the patient's face. In some embodiments, additional or secondary landmarks can be provided on the patient's face, such as by a marker pen, stickers (shown in FIG. 4B) and/or face masks. These additional landmarks can be used instead of or in combination with the three landmarks 401, 402, 403 or other suitable landmarks. Information about the landmarks 401, 402, 403 and other landmarks can be preloaded on a processor in communication with the smart injection system 200. The 9-axis IMS can communicate with the wireless transceiver 408 in any manner described above to provide angular and rotational position of a stem 410 coupled to a syringe 420 and a needle 430.

Figure 4C:
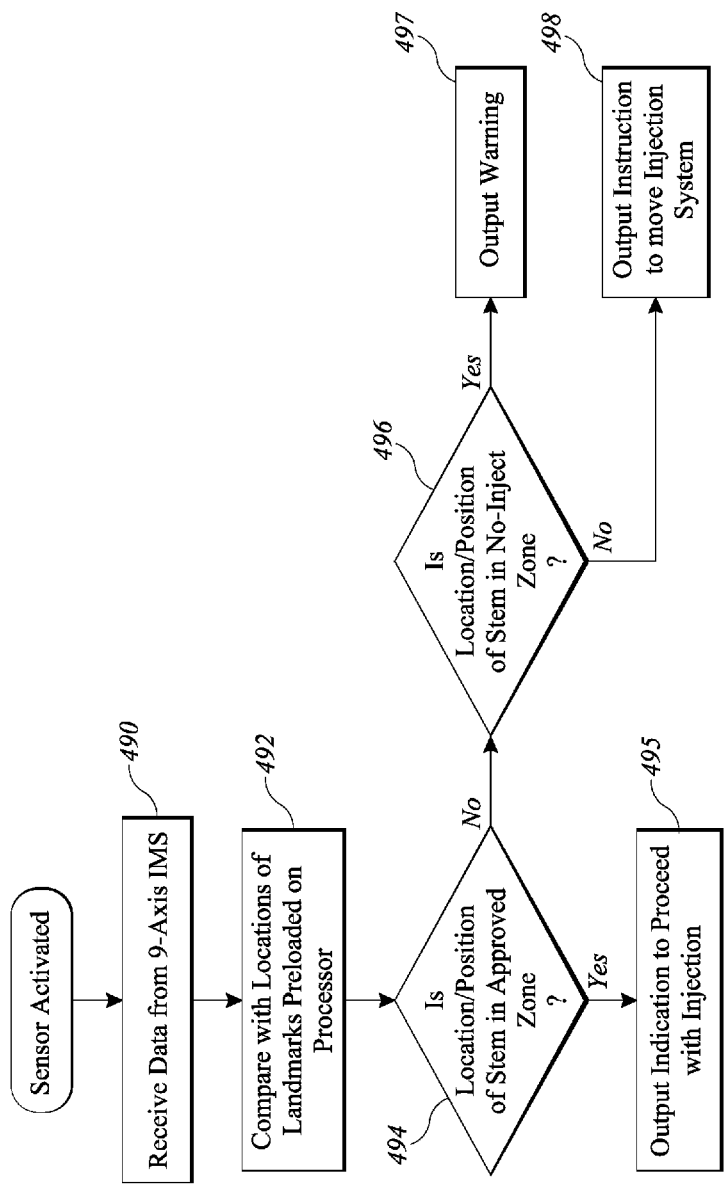
FIG. 4C illustrates another embodiment of a smart injection system with features for monitoring location of an injection site relative to the patient's face.

As shown in FIG. 4C, the processor can receive 490 data measured by the 9-axis IMS from the wireless transceiver 408 and compare 492 the measured data with the preloaded landmarks information in order to calculate the location and position of the injection system 400 relative to the patient's face. The processor can check 494 if the location is in an approved injection zone. If the injection system is in an approved zone, the processor can output an indication 495 that the caregiver can proceed with the injection at the current location and position of the injection system. If the injection system is not in an approved zone, the processor can check 496 if the injection system is in a no-injection zone. If the injection system is in a no-injection zone, the processor can output a warning 497 in any manner described herein. If the injection is in neither an approved nor a no-inject zone, the processor can output an instruction 498 to the caregiver to move the injection system.

In some embodiments, the processor can output an indication of the relative position of the injection system 400 to the patient's face by green and red LED lights. For example, a green light indicates that the injection system 400 is targeting an approved injection zone 405 and a red light indicates that the injection system 400 is targeting a no-inject zone 407. In another example, the processor can display the position of the injection system 400 relative to the patient's face on a display screen. Details of the display systems and methods are described in U.S. Provisional Application No. 62/303,251, filed Mar. 3, 2016 and entitled "GUIDED NEEDLE," the entirety of which is incorporated by reference herein and should be considered a part of this disclosure.

Integrated Smart Stem

Figure 5:
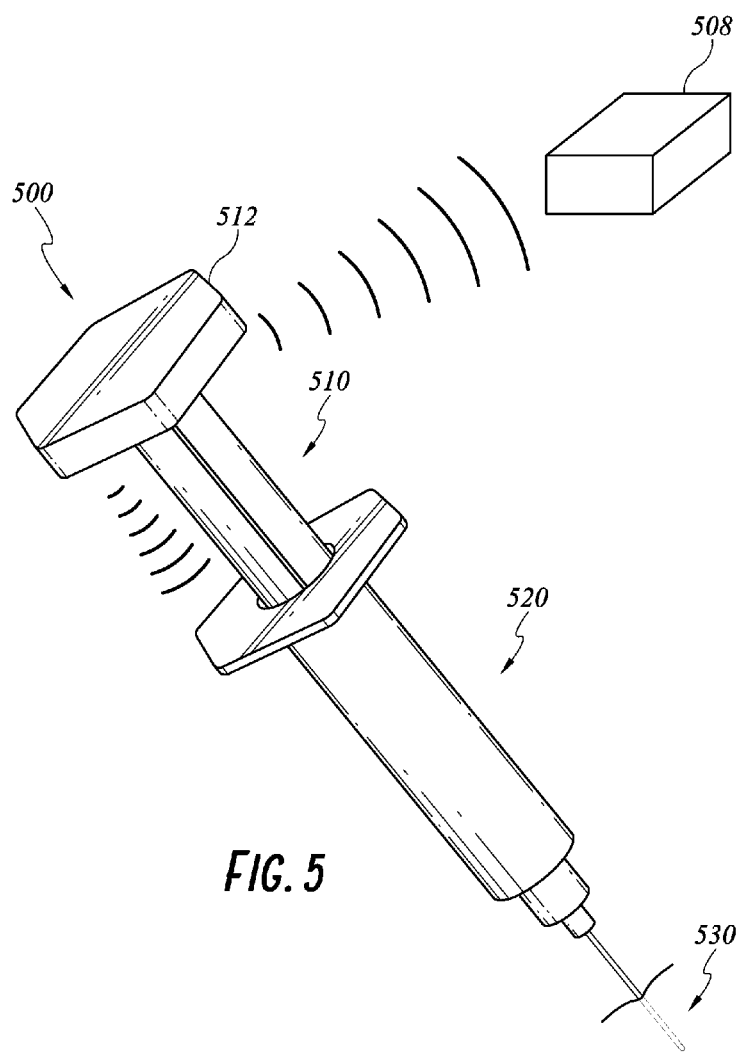
FIG. 5 illustrates another embodiment of the smart injection system with the electronics integrated into a stem cap.

Turning to FIG. 5, another embodiment of a smart injection system 500 will be described. The injection system 500 has the same features as the injection system 200, 400 except as described below. Accordingly, features of the injection system 200, 400 can be incorporated into features of the injection system 500 and features of the injection system 500 can be incorporated into features of the injection system 200, 400. The smart injection system 500 also has a stem 510, a syringe 520, and a needle 530. The syringe 520 and needle 530 may be standard off-the-shelf syringe and needle and be disposable. However, the stem 510 includes one or more electronic components as described above that are integrated into a proximal cap 512 of the stem 510. The stem 510 can be battery operated or rechargeable. Examples of the electronic components include but are not limited to force/pressure sensor, displacement sensor, 9-axis IMS, biometric sensor, power source and wireless transmitters. In this embodiment, the stem 510 is designed to be reusable. For example, some electronic components can be sealed within the proximal cap 512 so that the stem 510 can be sterilized without affecting those electronic components or any exposed sensors/readers can be directly sterilized. A skilled artisan will recognize that any method of using the injection system having the data cap 240 can be performed by the injection system 500 with the integrated proximal cap 512.

Smart Injection System with Medication Verification

Turning to FIG. 6A, a smart injection system 600 capable of verifying authenticity of a syringe containing certain medications will be described. The injection system 600 has the same features as the injection system 200, 400, 500 except as described below. Accordingly, features of the injection system 200, 400, 500 can be incorporated into features of the injection system 600 and features of the injection system 600 can be incorporated into features of the injection system 200, 400, 500.

In this embodiment, the syringe 620 can have a manufacturer's identification device 625 on the syringe shaft 624. The manufacturer's identification device 625 can be one or more of an EEPROM, a barcode, a RFID tag, or a resistor. The identification device 625 can be embedded in a wall of the syringe shaft 620, located on an inner or outer surface of the syringe shaft 624, or located at a top lip of the shaft, for example, as shown in FIG. 6C. Exact location of the identification device 625 on the syringe 220 is not limiting. The stem 610 has a corresponding identification device reader 615 on the stem shaft 614. For example, the corresponding identification device reader 615 can be an EEPROM reader, a bar code reader, an RFID tag reader or a resistance reader.

When an authentic syringe 620 prefilled with medication by the manufacturer is used with the stem 610, the identification device reader 615 on the stem 610 will interact with or read the identification device 625 on the syringe 620. For example, an RFID tag as the identification device 625 can be encoded by the manufacturer so that only an authentic prefilled syringe 620 will result in a positive reading. The identification device reader 615 on the stem 610 can be electrically wired to the wireless transmitter on the stem 210 and can provide a reading result to a wireless transceiver, which can forward the data to one or more remote servers. The injection system 600 or the wireless transceiver can provide a warning or indication of authenticity in any manner described above. The manufacturer can access information sent to the remote server receive to be informed when its medication is used and be alerted when a counterfeit prefilled syringe is detected by the stem 610.

In some embodiments, the identification device 625 can store information related to authenticity or product type, as well as optionally store information specific about the particular batch of medication or the syringe. Non-limiting examples of such information include serial and/or lot number, expiration date of the medication, and prior use of the syringe 620. Serial/Lot numbers can provide easy identification of the manufacturer and aid the manufacturer in keeping track of medication that has been injected into patients. Expiration date of the medication can ensure that patients are not injected with expired or unsafe products. Information about prior use of the syringe 620 can inform the caregiver and/or the patient that the medication in the syringe may have been tampered with and prevent cross-contamination caused by multiple uses of the syringe 620. The information can also be used for tracking inventory and aiding in product recalls.

Figure 6B:
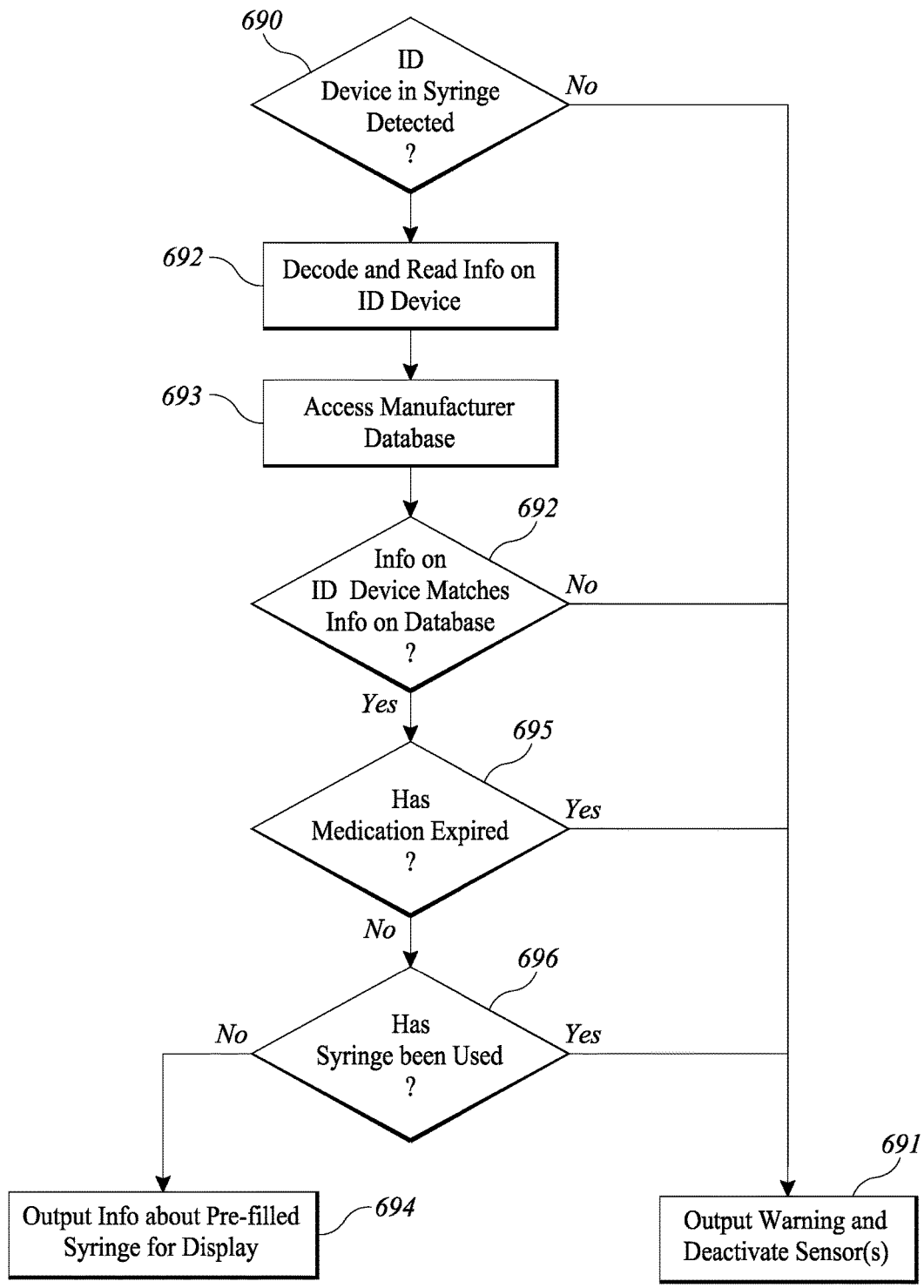
FIG. 6B illustrates an example flowchart of medication/syringe verification by the smart injection system of FIG. 6A.
Figure 6C:
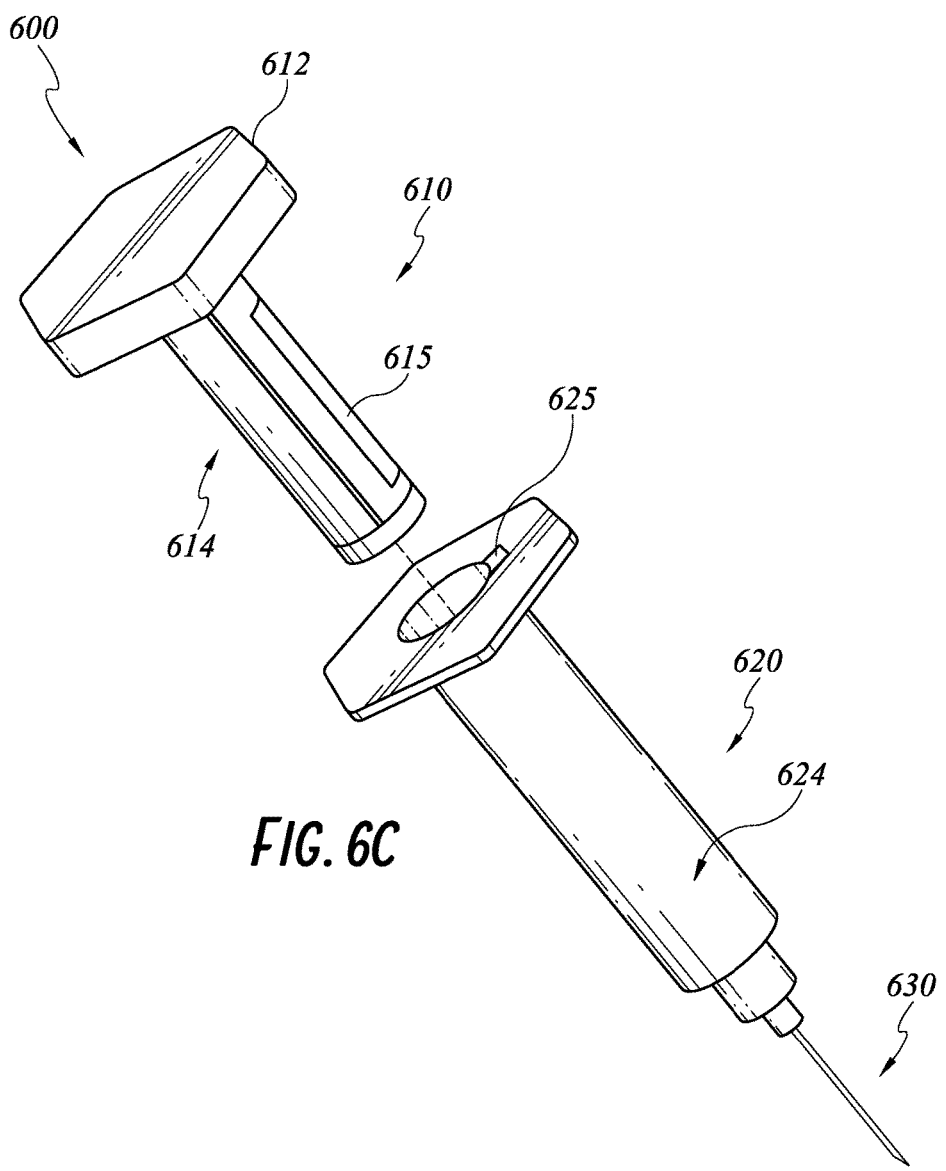
FIG. 6C illustrates another embodiment of a smart injection system with an identification device on a syringe and an identification device reader on a stem.

FIG. 6B illustrates a flowchart of processing activities of one or more processors. The processor first determines from the data sent by the identification device reader 615 if an identification device is present on the syringe 620 in step 690. In some embodiments, the identification device reader is powered by the electronic assembly of the injection system. In some embodiments, if no identification device is present, the processor will deactivate any sensors or readers on the electronic assembly so that no data about the counterfeit product is collected in step 691. The processor can also alert the patient, caregiver, and/or the manufacturer about counterfeit products in the step 691. In an embodiment, sensors can continue to operate, but the data is not provided to the physician. It can be kept for later analysis by the manufacturer. In other embodiments, only an alert is provided, but the processor and sensors continue to operate as normal. If an identification device is present and can be read, the processor can optionally decode 692 any encoded information on the identification device. Once the information has been decoded, the processor can access a manufacturer's database 693 containing information about its prefilled syringes to compare the decoded information with information on the database. If there is a match between the data on the syringe and information on the database, the processor can output for display 694 the information about the prefilled syringe, such as the manufacturer information, serial and lot numbers, product types, instructions for use, indications, etc., and output an indication that the prefilled syringe is an authentic product. If there is no match, the processor can repeat the warning step 691. The processor can optionally further determine if the medication has expired based on its date of production 695, or if the syringe has been previously used 696, which suggests that the syringe and the medication in the syringe has been tampered with. The processor can then output either an indication that the prefilled syringe is safe for use 694 or a warning 691 accordingly.

Smart Stem with Injector Verification

In some embodiments, the smart injection system described herein can optionally include a biometric sensor. The biometric sensor can be included on the data cap 240, for example, on the PCB 250, or on the integrated proximal cap 512 of the stem 510. A non-limiting example of biometric sensors is a fingerprint reader, although a skilled artisan will recognize that other biometric sensors known in the art can be used. The biometric sensor can detect information about the person performing the injection procedure. The biometric sensor can transmit measured data about the person performing the injection procedure to the wireless transceiver 208, 508, which can in turn send the measured data to a processor in communication with the wireless transceiver. In some embodiments, the processor can be on a remote server, which can also store or have access to a database of qualified personnel.

Figure 7:
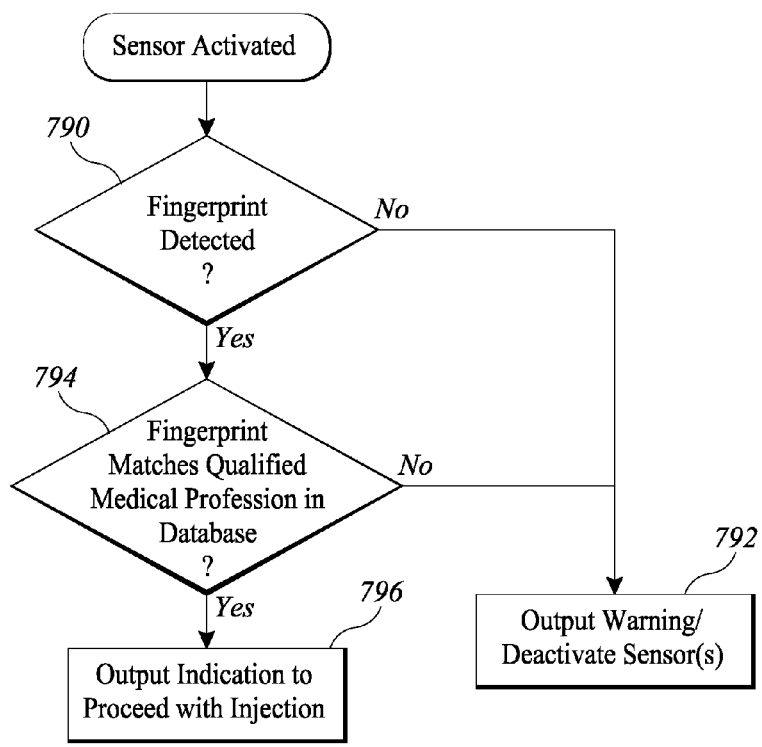
FIG. 7 illustrates an example flowchart of injector verification by an embodiment of a smart injection system.

As shown in FIG. 7, the processor can first determine if any data is read 790 by the biometric sensor after the smart injection system has been activated. The processor can output a warning 792 if the biometric sensor cannot read any data and/or stop all measuring activities as described herein. In some embodiments, the processor can also deactivate all sensors of the electronic assembly so that no data about the injection procedure is measured in the warning step 792. In some embodiments, the warning step 792 can further include a warning to the medical certification board that the clinic or hospital where the injection took place is likely allowing unqualified personnel to perform the injection. If biometric data about the injector is received, the processor compares it with the database of qualified personnel 794 to look for a match. If the data collected about the person performing the injection does not match one in the database, the processor can repeat the alert step 792 described herein. If there is a match, the processor can output an indication that the injector is qualified to perform the injection 796. Collecting data about the caregiver can deter clinics/hospitals from hiring untrained staff to perform the injections, thereby improving safety of the patients and accountability of the medical professionals.

Integrated Syringe Flange

Figure 8A:
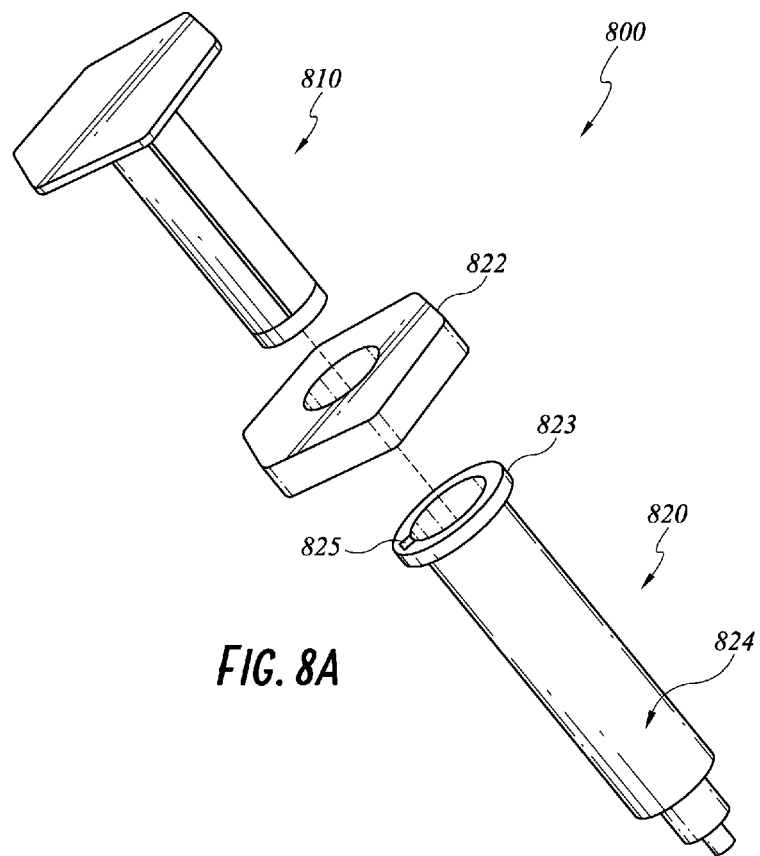
FIG. 8A illustrates an exploded view of another embodiment of a smart injection system with the electronics integrated in a syringe flange.
Figure 8B:
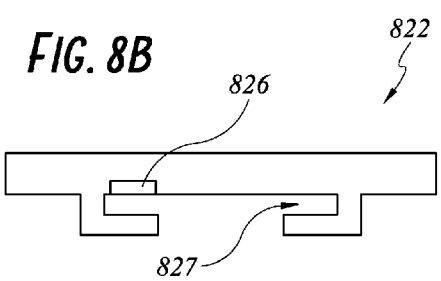
FIG. 8B illustrates a side view of the syringe flange of FIG. 8A.

Turning to FIGS. 8A-B, another embodiment of a smart injection system 800 will be described. The injection system 800 has the same features as the injection system 200, 400, 500, 600, except as described below. Accordingly, features of the injection system 200, 400, 500, 600, can be incorporated into features of the injection system 800 and features of the injection system 800 can be incorporated into features of the injection system 200, 400, 500, 600. The smart injection system 800 has a stem 810, a flange 822, and a syringe 820 with a syringe lip 823 and a syringe shaft 824. A needle can be coupled to the syringe shaft 824 at a distal end of the syringe shaft 824.

FIG. 8A-8B illustrate an example mechanism for removably coupling the flange 822 to the syringe 820. As shown, the flange 822 has a slot 827 sized to fit the syringe lip 823. Sliding the syringe lip 823 into the slot 827 allows the flange 822 to be attached to the syringe 820. A skilled artisan will recognize that other means of coupling the flange 822 to the syringe 820 known in the art, for example, clips, adhesives, and the like, can be used without departing from the scope of the disclosure herein.

The stem 810 and the syringe 820 may be standard off-the-shelf parts, and be disposable. The flange 822 includes one or more electronic components as described above that are integrated into the flange 822 and is designed to be reusable. In this embodiment, for example, some electronic components can be sealed within the flange 822 so that the flange 822 can be sterilized without affecting those electronic components or any exposed sensors/readers can be directly sterilized.

Examples of the electronic components include but are not limited to a velocity sensor, a 9-axis IMS, biometric sensor, an identification device reader, a power source (for example, disposable or rechargeable batteries), and wireless transmitters. For example, the velocity sensor can be any velocity sensor known in the art and can measure the displacement and/or rate of displacement of the stem 810 relative to the syringe 820. Information about the speed of injection and volume of medication injected into the patient can be determined with the data measured by the velocity sensor as described above. In addition, the injection pressure can be calculated based on the measured data and known constants, including but not limited to viscosity and drag. A skilled artisan will recognize that the velocity sensor can be implemented in the data cap 240 and/or the integrated stem 510. A skilled artisan will also recognize that any method of using the injection system having the data cap 240 or the integrated stem proximal cap 512 can be performed by the injection system 800 with the integrated flange 822. It is to be understood that only one, more than one, or all of the above listed sensors and other sensors known in the art can be integrated into and used with flange 822.

In some embodiments, an identification device 825 as described above can be placed on the syringe lip 823, as shown in FIG. 8A. When the flange 822 connects to the syringe lip 823, an identification device reader 826 on the flange 823 can read the information on the identification device 825 in any manner described herein and perform verification of the medication prefilled in the syringe 820 and/or the syringe 820.

Combination and/or Subcombination Embodiments

Although features of the smart injection system are described individually in various embodiments herein, a skilled artisan will appreciate that any one or more of those features described herein can be implemented on a smart injection system.

Figure 9:
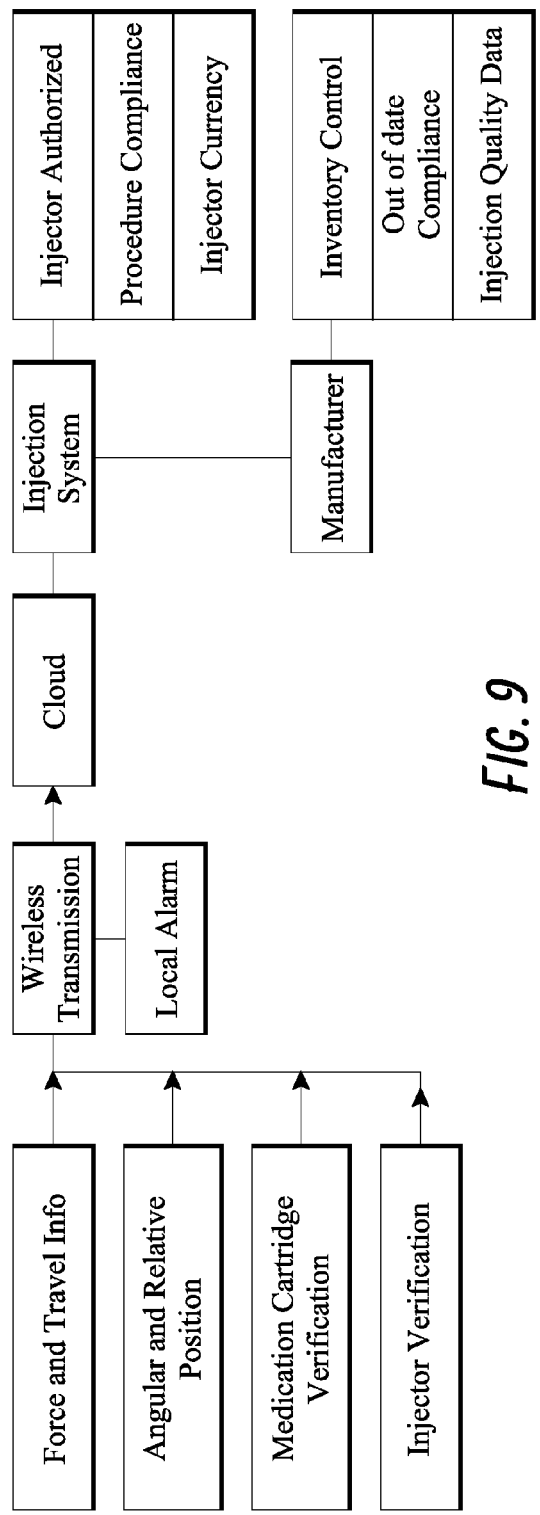
FIG. 9 illustrates examples of integrating features of a smart injection system.

An example combination of features and the advantages thereof are illustrated in FIG. 9. The injection system can have an electronic assembly configured to measure a variety of information, including but not limited to force of injection and/or travel of the stem information, angular and relative position of the stem relative to a patient's face, verify authenticity and other product information of a prefilled syringe, and verify identity of an injector, in the manners described above. The information measured by the electronic assembly can be transmitted to one or more processors located locally or remotely. In some embodiments, the measured data can cause the one or more processors to generate local alerts/alarms on the injection system or in the room where the patient receives the injection. In some embodiments, data transmission can be performed wirelessly and the one or more processors can be located on one or more remote servers (the "Cloud"). In response to the measured data, the processor can output instructions to the injection system. Examples of the instructions include information about whether the injector is an authorized/licensed medical professional, whether the procedure is in compliance with protocols, whether the medication being injected is safe and/or authentic, and the like. In response to the measured data, the processor can also output alerts and/or data to the manufacturer, including but not limited to information about medication usage for inventory control, monitoring of injectors' qualification, and injection quality data. In some embodiments, the processor can make the alerts and/or data available for retrieval by the manufacturer. In other embodiments, the processor can automatically send the alerts and/or data to the manufacturer.

In addition, an augment to the alarms/alerts on the injection system can provide audio, visual or tactile feedback confirming the correct injection technique. This continuous feedback contributes to a more perfect injection than threshold alarms that are triggered only at the limits of acceptable operation.

It is to be understood that the various sensor and electronics, as well as the techniques and processes described with respect to each embodiment disclosed herein can be used with and integrated to other embodiments disclosed herein as would be readily understood by a person of skill in the art reading the present disclosure.

Terminology

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication. For example, actions such as "inserting the testing tool" include "instructing insertion of a testing tool."

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on general purpose computer hardware, or combinations of both. Various illustrative components, blocks, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. An injection system, the system comprising:
a syringe including a stem, a barrel, and a needle, wherein the stem comprises a proximal cap and a shaft, the shaft configured to engage a lumen of the barrel from a proximal end of the barrel, a distal end of the barrel configured to couple to the needle, and wherein the needle is configured to penetrate skin of a patient to inject medication contained in the syringe to a patient;
a reusable electronic assembly configured to be coupled to at least a portion of the syringe; and
a displacement sensor located on or near a distal end of the proximal cap of the stem, the displacement sensor configured to send one or more optical signals to a reflecting surface on the barrel and receive one or more reflected optical signals, wherein the electronic assembly is configured to use inputs from the displacement sensor to measure data including injection speed, displacement of the stem relative to the barrel, a volume of medication injected, and/or a medication flow rate of an injection using the syringe, and wherein the electronic assembly is configured to communicate with a hardware processor, the hardware processor configured to process the data measured by the electronic assembly to output feedback on the infection.

2. The injection system of claim 1, wherein the reflecting surface is on a proximal flange of the barrel.

3. The injection system claim 1, further comprising a force or pressure sensor located on the proximal cap of the stem, the force or pressure sensor configured to measure data about a force or pressure applied on the proximal cap.

4. The injection system of claim 1, further comprising an identification device on the barrel and a corresponding identification device reader on the shaft to measure an indication of authenticity of medication, the corresponding identification device reader interacting with the identification device when the stem is pushed distally into the lumen.

5. The injection system of claim 1, wherein at least a portion of the electronic assembly is located on a snap-on data cap configured to be coupled with the proximal cap of the stem.

6. The injection system of claim 1, further comprising the hardware processor, wherein the hardware processor is on a remote server.

7. An injection system, the system comprising:
a syringe including a stem, a barrel, and a needle, the stem comprising a proximal cap and a shaft, the shaft configured to engage a lumen of the barrel from a proximal end of the barrel, and a distal end of the barrel configured to couple to the needle, wherein the needle is configured to penetrate skin of a patient to inject medication contained in the syringe to a patient;
a reusable electronic assembly configured to be coupled to at least a portion of the syringe; and
a displacement sensor located on or near a distal end of the proximal cap of the stem, the displacement sensor configured to send one or more acoustic signals to a reflecting surface on the barrel and receive one or more reflected acoustic signals, wherein the electronic assembly is configured to use inputs from the displacement sensor to measure data including injection speed, displacement of the stem relative to the barrel, a volume of medication injected, or a medication flow rate of an injection using the syringe, and wherein the electronic assembly is configured to communicate with a hardware processor, the hardware processor configured to process the data measured by the electronic assembly to output feedback on the injection.

8. The injection system of claim 7, wherein the reflecting surface is on a proximal flange of the barrel.

9. The injection system of claim 7, wherein at least a portion of the electronic assembly is located on a snap-on data cap configured to be coupled with the proximal cap of the stem.

10. The injection system of claim 7, further comprising a force or pressure sensor located on the proximal cap of the stem, the force or pressure sensor configured to measure data about a force or pressure applied on the proximal cap.

11. The injection system of claim 7, further comprising the hardware processor, wherein the hardware processor is on a remote server.

12. The injection system of claim 7, further comprising an identification device on the barrel and a corresponding identification device reader on the shaft to measure an indication of authenticity of medication, the corresponding identification device reader interacting with the identification device when the stem is pushed distally into the lumen.

13. An injection system, the system comprising:
a syringe including a stem, a barrel, and a needle, the stem comprising a proximal cap and a shaft, the shaft configured to engage a lumen of the barrel from a proximal end of the barrel, and a distal end of the barrel configured to couple to the needle, wherein the needle is configured to penetrate skin of a patient to inject medication contained in the syringe to a patient;
a reusable electronic assembly configured to be coupled to at least a portion of the syringe;
a displacement sensor located on or near a distal end of the proximal cap of the stem, the displacement sensor configured to send one or more optical or acoustic signals to a reflecting surface on the barrel and receive one or more reflected optical or acoustic signals, wherein the electronic assembly is configured to use inputs from the displacement sensor to measure injection speed, displacement of the stem relative to the barrel, a volume of medication injected, or a medication flow rate of the injection; and
a biometric sensor located on or near the distal end of the proximal cap of the stem,
wherein the electronic assembly is configured to use inputs from the biometric sensor to measure biometric data of a person performing an injection using the syringe, and
wherein the electronic assembly is configured to communicate with a hardware processor, the hardware processor configured to process the biometric data measured by the electronic assembly to output feedback on the injection.

14. The injection system of claim 13, wherein the biometric sensor comprises a fingerprint reader.

15. The injection system of claim 13, wherein at least a portion of the electronic assembly is located on a snap-on data cap configured to be coupled with the proximal cap of the stem.

16. The injection system of claim 13, wherein the reflecting surface is on a proximal flange of the barrel.

17. The injection system of claim 13, further comprising a force or pressure sensor located on the proximal cap of the stem, the force or pressure sensor configured to measure data about a force or pressure applied on the proximal cap.

18. The injection system of claim 13, further comprising the hardware processor, wherein the hardware processor is on a remote server.

19. The injection system of claim 13, further comprising an identification device on the barrel and a corresponding identification device reader on the shaft to measure an indication of authenticity of medication, the corresponding identification device reader interacting with the identification device when the stem is pushed distally into the lumen.

* * * * *

UNITED STATES PATENT AND TRADEMARK OFFICE
CERTIFICATE OF CORRECTION

PATENT NO. : 10,500,340 B2
APPLICATION NO. : 15/299209
DATED : December 10, 2019
INVENTOR(S) : Gabrielle A. Rios et al.

Page 1 of 1

It is certified that error appears in the above-identified patent and that said Letters Patent is hereby corrected as shown below:

In the Specification

In Column 11, Line 7, delete "and or" and insert --and/or--.

In Column 15, Line 57, delete "FIG." and insert --FIGS.--.

In the Claims

In Column 20, Lines 10-11, in Claim 1, delete "infection." and insert --injection.--.

In Column 20, approximately Line 14, in Claim 3, after "system" insert --of--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*